(12) United States Patent
Zettl et al.

(10) Patent No.: US 8,674,134 B2
(45) Date of Patent: Mar. 18, 2014

(54) OLIGOMER FUNCTIONALIZED NANOTUBES AND COMPOSITES FORMED THEREWITH

(75) Inventors: Alexander K. Zettl, Kensington, CA (US); Toby Sainsbury, Dublin (IE); Jean M. J. Fréchet, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 152 days.

(21) Appl. No.: 13/162,422

(22) Filed: Jun. 16, 2011

(65) Prior Publication Data

US 2012/0088934 A1 Apr. 12, 2012

Related U.S. Application Data

(60) Provisional application No. 61/355,722, filed on Jun. 17, 2010.

(51) Int. Cl.
 *C07C 233/65* (2006.01)
 *B82Y 40/00* (2011.01)
 *B82Y 30/00* (2011.01)

(52) U.S. Cl.
 USPC ........... 564/153; 564/155; 564/156; 564/188; 977/705; 977/748; 977/750; 977/752; 977/755; 977/847; 977/896

(58) Field of Classification Search
 USPC .......... 564/155, 156, 188; 977/705, 748, 750, 977/752, 755, 847, 896
 See application file for complete search history.

(56) References Cited

U.S. PATENT DOCUMENTS

| | | | |
|---|---|---|---|
| 6,368,569 | B1 | 4/2002 | Haddon et al. |
| 7,125,533 | B2 | 10/2006 | Khabashesku et al. |
| 7,384,520 | B2 | 6/2008 | Iijima et al. |
| 2001/0023021 | A1 | 9/2001 | Cohen et al. |
| 2004/0058457 | A1 * | 3/2004 | Huang et al. ................. 436/524 |
| 2007/0183959 | A1 | 8/2007 | Charlier et al. |
| 2008/0008760 | A1 | 1/2008 | Bianco et al. |
| 2008/0093211 | A1 | 4/2008 | Ramanath et al. |
| 2010/0051879 | A1 | 3/2010 | Sainsbury et al. |

FOREIGN PATENT DOCUMENTS

WO  WO 03/080513  * 10/2003

OTHER PUBLICATIONS

Dehonor, et al., "Nanotube brushes: polystyrene grafted covalently on CNx nanotubes by nitroxide-mediated radical polymerization", Chem. Commun., 2005, 5349-5351.
Chen, et al., "Novel boron nitride hollow nanoribbons", ACS Nano, 2008, 2 (10), 1283-2191.
Sainsbury, et al., "Kevlar functionalized carbon nanotubes for next-generation composites", Chem. Mater. 2010, 22, 2164-2171.
Cai, et al., "Atomically precise bottom-up fabrication of graphene nanoribbons", Nature, vol. 466, Jul. 22, 2010 pp. 470-473.
Balasubramanian, et al., "Chemically functionalized carbon nanotubes", Small, 2005, 1, No. 2, 180-192.

* cited by examiner

*Primary Examiner* — Shailendra Kumar
(74) *Attorney, Agent, or Firm* — David J. Aston; Peters Verny, LLP

(57) ABSTRACT

Disclosed herein is a sequential functionalization methodology for the covalent modification of nanotubes with between one and four repeat units of a polymer. Covalent attachment of oligomer units to the surface of nanotubes results in oligomer units forming an organic sheath around the nanotubes, polymer-functionalized-nanotubes (P-NTs). P-NTs possess chemical functionality identical to that of the functionalizing polymer, and thus provide nanoscale scaffolds which may be readily dispersed within a monomer solution and participate in the polymerization reaction to form a polymer-nanotube/polymer composite. Formation of polymer in the presence of P-NTs leads to a uniform dispersion of nanotubes within the polymer matrix, in contrast to aggregated masses of nanotubes in the case of pristine-NTs. The covalent attachment of oligomeric units to the surface of nanotubes represents the formation of a functional nanoscale building block which can be readily dispersed and integrated within the polymer to form a novel composite material.

23 Claims, 15 Drawing Sheets

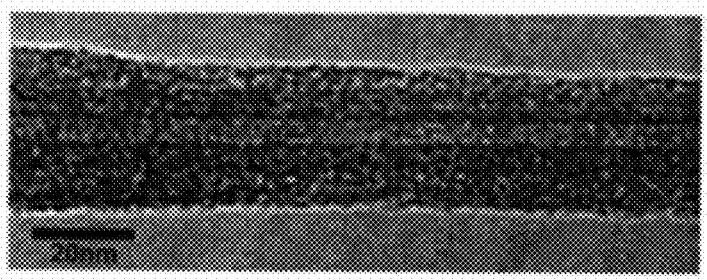
*FIG. 5*
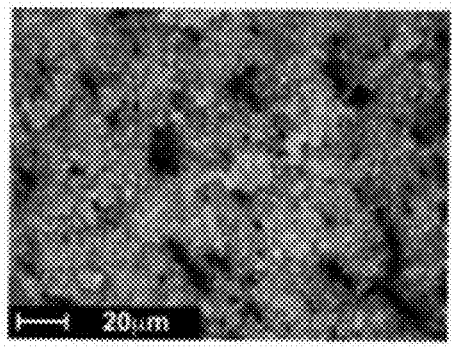 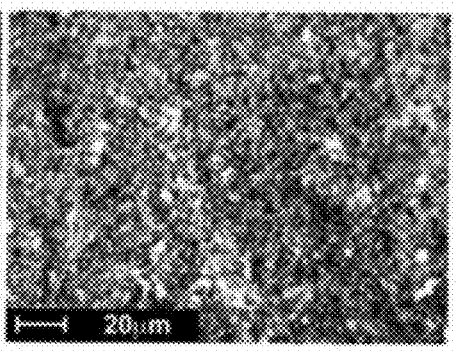
*FIG. 6A*    *FIG. 6B*
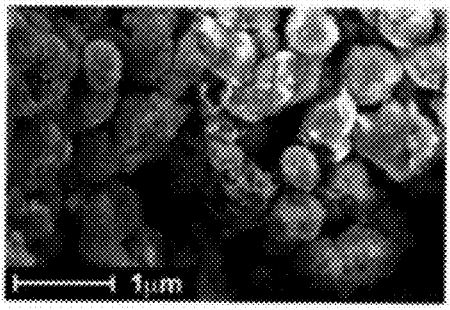 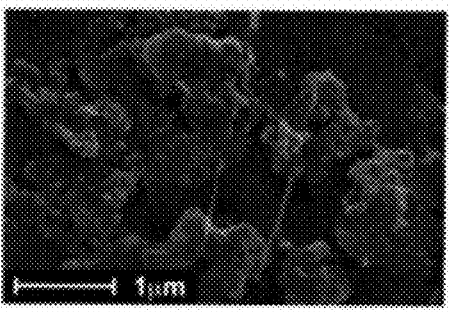
*FIG. 6C*    *FIG. 6D*
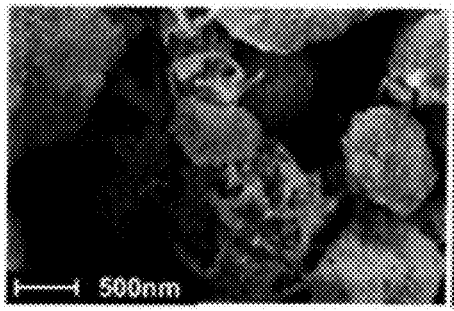 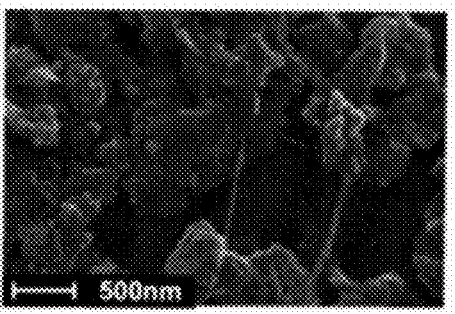
*FIG. 6E*    *FIG. 6F*

OLIGOMER FUNCTIONALIZED NANOTUBES AND COMPOSITES FORMED THEREWITH

CROSS-REFERENCE TO RELATED APPLICATIONS

This application claims priority from U.S. Provisional Patent Application No. 61/355,722, filed Jun. 17, 2010, which is hereby incorporated by reference in its entirety.

STATEMENT OF GOVERNMENTAL SUPPORT

This invention was made with U.S. Government support under Contract Number DE-AC02-05CH11231 between the U.S. Department of Energy and The Regents of the University of California for the management and operation of the Lawrence Berkeley National Laboratory. The U.S. Government has certain rights in this invention.

REFERENCE TO SEQUENCE LISTING, COMPUTER PROGRAM, OR COMPACT DISK

None.

BACKGROUND OF THE INVENTION

1. Field of the Invention

The present invention relates to the field of materials and particularly to compositions and methods for oligomer functionalized nanotubes and composites thereof.

2. Related Art

Presented below is background information on certain aspects of the present invention as they may relate to technical features referred to in the detailed description, but not necessarily described in detail. That is, individual parts or methods used in the present invention may be described in greater detail in the materials discussed below, which materials may provide further guidance to those skilled in the art for making or using certain aspects of the present invention as claimed. The discussion below should not be construed as an admission as to the relevance of the information to any claims herein or the prior art effect of the material described.

Carbon Nanotubes (CNTs) have stimulated intense research interest in recent years on account of their unique physical properties. A significant proportion of this research has been directed towards the use of these 1-D nanoscale materials as fillers in polymer composite materials.[1-3] (A list of publications corresponding to the numbers in superscripts is attached at the end of the disclosure). Many of these reports have documented remarkable advances in the formation of hybrid materials which exhibit extreme high modulus and strength values far exceeding those of conventional high performance materials.[4-6] New synthetic methodologies for nanotube production now allow the preparation of ultra-high aspect-ratio nanotubes which may be impregnated within polymer matrices to yield novel composites.[7,8] Consequently, the paradigm shift in material properties promised by research involving nanoscale structures is slowly becoming a realization.[9-11] Some nanotube-based advances have utilized developments in the physical properties of carbon nanotubes, such as increases in length, control over diameter, and the ability to prepare precisely controlled arrays of free-standing nanotubes on a range of substrates.[9,12,13] In parallel with this, progress has been made in the chemical functionalization of carbon nanotubes and their successful integration within polymer matrices to yield significantly improved composite materials.[14-16]

While much has been achieved, the issue of successfully integrating nanotubes within polymers at volume fractions whereby the efficiency of stress transfer between the tubes and the polymer matrix is optimized remains at large. Resolving this issue by combining optimized physical properties with precisely controlled chemical functionality would be expected to yield even further improvement in mechanical properties in such composites, while greater interfacial interaction would be expected to facilitate significantly improved electronic and thermal management characteristics of such materials.[16] Towards this end, discrete molecules, polymerization initiators, and polymers have been grafted to and from the surface of carbon nanotubes.[17-20] However, relatively few reports exist concerning the tailored grafting of short-chain analogues of the host polymer matrix to the surface of nanotubes.

SPECIFIC PATENTS AND PUBLICATIONS

U.S. Patent Application Publication 20080093211, published Apr. 24, 2008, by Ramanath et al., "Method for site-selective functionalization of carbon nanotubes and uses thereof", discloses a method of functionalizing a carbon nanotube which includes providing a nanotube, irradiating at least one exposed portion of the nanotube surface with ions to generate defect sites on the at least one exposed portion, and forming at least one functional group at a defect site.

Dehonor, et al., "Nanotube brushes: polystyrene grafted covalently on $CN_x$ nanotubes by nitroxide-mediated radical polymerization" Chem. Commun., 2005, 5349-5351, discloses the synthesis of polystyrene brushes attached to N-doped multiwalled carbon nanotubes via in situ nitroxide-mediated radical polymerization.

U.S. Pat. No. 7,125,533 to Khabasheshku et al., issued on Oct. 24, 2006, discloses a method for functionalizing the wall of single-wall or multi-wall carbon nanotubes which involves the use of acyl peroxides to generate carbon-centered free radicals.

Liu, "Modifications of carbon nanotubes with polymers," European Polymer Journal, Volume 41, Issue 11, November 2005, Pages 2693-2703, discloses that SWNTs may be non-covalently associated with a variety of linear polymers such as polyvinyl pyrrolidone (PVP) and polystyrene sulfonate (PSS). Conjugated luminescent polymer poly-(m-phenylenevinylene)-co-[(2,5-dioctyloxy-p-phenylene)-vinylene] (PmPV) and its derivatives, such as poly (2,6-pyridinylenevinylene)-co-[(2,5-dioctyloxy-p-phenylene)vinylene] (PPyPV) and poly (5-alkoxy-m-phenylenevinylene)-co-[(2,5-dioctyloxy-p-phenylene)-vinylene] (PAm PV), had been successfully used for the wrapping around SWNTs on account of stabilizing noncovalent bonding interactions, presumably as a result of π-π stacking and van der Waals interactions between PmPV and the surfaces of the SWNTs.

Kitano et al., "Functionalization of single-walled carbon nanotube by the covalent modification with polymer chains," Journal of Colloid and Interface Science Volume 306, Issue 1, 1 Feb. 2007, Pages 28-33 (available on line 24 Oct. 2006) discloses that a single-walled carbon nanotube (SWNT), which had been oxidized by incubation with a mixture of nitric acid and sulfuric acid to afford carboxyl groups at its ends, was incubated with an azo-type radical initiator carrying poly(2-methacryloyloxyethyl d-glucopyranoside) blocks at both ends (PMEGlc-initiator). Due to its high radical trapping activity, the SWNT could be coated with glycopolymers corresponding to the cloven macro-initiator (PMEGlc-SWNT). The PMEGlc-SWNT indicated a lectin (concanavalin A, Con A)-induced aggregation, and a buckey sheet composed of PMEGlc-SWNT could be used for the recovery of Con A from its aqueous solution.

BRIEF SUMMARY OF THE INVENTION

The following brief summary is not intended to include all features and aspects of the present invention, nor does it imply that the invention must include all features and aspects discussed in this summary.

In certain aspects of the present invention, nanotubes are specifically functionalized to adopt chemical properties identical to those of a polymer matrix (e.g. functionalized with amide oligomer in a polyamide polymer) and, furthermore, to allow surface bound reactive chemical groups to facilitate the nature of the interaction between tubes and matrix or substrate. In particular, CNTs functionalized specifically with chemistries identical to their intended host matrix of a composite are disclosed.

Disclosed herein are methods of preparation and compositions relating to composite materials comprising nanostructures. Embodiments of the invention are related to a nanostructure material comprising (a) a nanostructure having a defined pattern of covalently bonded surface atoms; (b) linking groups covalently bonded to a portion of said surface atoms; and (c) aromatic polyamide attached by the linking groups to the nanostructure. Nanostructures embodied by the present invention may comprise a graphene surface structure and include carbon nanotubes, including single-walled nanotubes (SWNT), multiwalled nanotubes (MWNT), double-walled nanotubes (DWNT), boron nitride nanotube, BxCyNz nanotube where x, y, and z indicate a relative amount of each element compared to the others and where no more than one of x, y, or z are zero for a single stoichiometry, graphene sheet, graphene ribbon and silicon nanotube.

In some embodiments, the linking groups are selected from a group consisting of a carboxylic acid, an aster, an acyl halide, an amine, an acyl amide and a sulfide. The linking groups may have the formula —C(=O)—, with a first carbon bond to the nanostructure and a second carbon bond to a monomer of the oligomer. The second carbon bond may be to an amine group on the monomer. In one embodiment, the monomer is p-phenylenediamine (PDA).

The aromatic polyamide possesses between two and twenty monomer units. In some embodiments, the aromatic polyamide comprises an aromatic diamine and an aromatic diacyl chloride. In other embodiments, the aromatic polyamide comprises alternating monomers of different chemical structure. In yet another embodiment, the aromatic polyamide comprises monomers of PDA and terephthaloyl chloride (TPC).

Some embodiments are related to a nanostructure material comprising (a) a nanostructure having a defined pattern of covalently bonded surface atoms; (b) linking groups covalently bonded to at least 1% of said surface atoms; and (c) one or more (e.g. up to 10) monomers of an aromatic polyamide attached by the linking groups to the nanostructure. The nanostructure may be a carbon nanotube. The linking groups may comprise carbonyl atoms. The material may be dispersed into a polymer matrix comprising monomers having the same chemical structure as the aromatic polyaramid attached by the linking group(s) to the nanostructure.

Embodiments of the present invention are directed to a composite material comprising a polyamide matrix in which is embedded a nanostructure material, comprising (a) a nanostructure having a defined pattern of covalently bonded surface atoms; (b) linking groups covalently bonded to a portion of said surface atoms; and (c) synthetic oligomers attached by the linking groups to the nanostructure. In some embodiments, the synthetic oligomers have the same structure as the polyamide matrix. In some embodiments, the polyamide matrix comprises cross links to the synthetic oligomers. In one embodiment, the crosslinks are hydrogen bonds between aromatic residues on the oligomers and the polyamide matrix.

The present invention also embodies methods of preparation of a nanostructure material comprising the steps of: (a) suspending nanostructures in a fluid; (b) reacting the nanostructures in the fluid with a strong oxidizer for attachment of linking groups to form functionalized nanostructures; (c) reacting the functionalized nanostructures with a first monomer unit to link the monomer unit to the linking groups and form a monomer-nanostructure; and (d) adding a second monomer unit to said monomer-nanostructure under conditions to couple the second monomer unit to the first monomer unit to form a copolymer after coupling. The first monomer unit and the second monomer unit independently comprise one-, two- or three-mers of monomer. In some embodiments, the conditions that couple the second monomer unit to the first monomer unit comprise a condensation reaction.

In some embodiments, the first monomer unit is a monomer of an aromatic diamine. In some other embodiments, the second monomer unit is a monomer of an aromatic diacyl chloride. In some embodiments, the first and second monomer units may be reacted as a mixture of monomer units to yield a random copolymer.

In some embodiments, the method may further comprise the step of adding a pre-formed oligomer of two to five units to the nanostructure.

BRIEF DESCRIPTION OF THE DRAWINGS

FIG. 5 is a high resolution transmission electron microscopy image of a PDA-TPC-PDA-functionalized MWNT, indicating a monolayer of PPTA-oligomer material surrounding the MWNT.

FIG. 6a-f is a set of optical and scanning electron microscopy images of p-MWNT/PPTA composites (FIGS. 6a, 6c, and 6e) and PPTA-MWNT/Kevlar® aramid fiber (FIGS. 6b, 6d, and 6f).

DETAILED DESCRIPTION OF THE PREFERRED EMBODIMENT

Definitions

Figure 1:
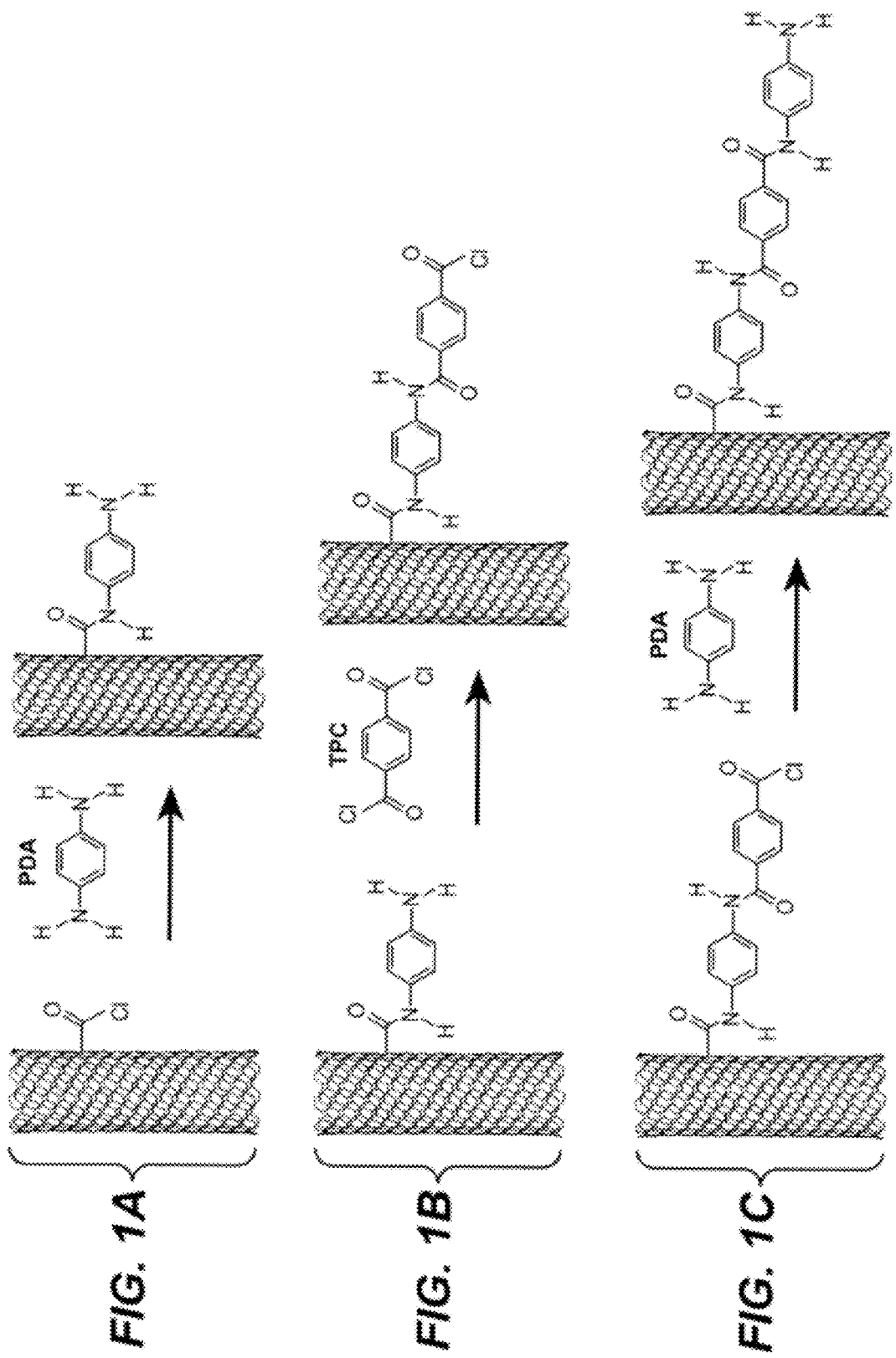
FIG. 1a-c is a scheme for sequential functionalization of MWNTs with poly-p-phenyleneterephthalamide (PPTA) monomer units; 1a shows PDA coupling; 1b shows TPC coupled to the PDA; and 1c shows further coupling with PDA.

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, physics, material science and chemistry are those well known and commonly used in the art. Certain experimental techniques, not specifically defined, are generally performed according to conventional methods well known in the art and as described in various general and more specific references that are cited and discussed throughout the present specification. For purposes of the clarity, following terms are defined below.

The term "nanostructure" is used herein to refer to structures which have a size between molecular and micron-sized structures. Typically, such structures have at least one dimension on the nanoscale, e.g., between about 1 nm and about 100 nm. The nanostructures can be configured so as to include one or more of the following: (1) a nano surface having one dimension on the nanoscale, for example, a surface thickness between 1 nm and 100 nm; (2) a nanotube having two dimensions on the nanoscale, for example, a diameter and length each between 1 nm and 100 mm; and (3) a nanoparticle having three dimensions on the nanoscale, for example, the three spatial dimensions of the nanoparticle being between 1 nm and 100 nm.

A "nanotube" is a nanostructure having a length at least ten times its diameter. The nanostructure may exhibit optimum properties with a length between 10 micron and 10 nanometers and a diameter between 0.5 nm and 100 nm. A "nanostructure" as used herein is essentially atomically smooth, having mechanical defects essentially only at places where inertial clamps may be desired. The present nanostructure may contain a mixture of materials, or may be essentially pure, or contain dopants, e.g., carbon doped with Ge, B, P, As, Ge, Ga, In, or Al. The term "nanostructure" includes nanotubes, nanospheres, nanowires, nanorods, and nanodisks (see Gao et al., "Spiral Spin Order of Self-Assembled Co Nanodisk Arrays," Phys. Rev. Lett. 96, 137205 (2006)). In the case of non-elongated nanostructures used as resonators, oscillation may be induced by expansion and contraction of the nanostructure, or a torsional movement.

The term "nanotube" is used here in a broad sense to include single-walled nanotubes, multiwalled nanotubes, etc. Other forms of nanotube may be used, so long as they have uniform mechanical properties and are chemically inert to the atoms that are to be transported and used to form the inertial clamps. The term nanotube particularly includes carbon nanotubes. These may consist of one tube of graphite, a one-atom thick single-wall nanotube (SWNT), or a number of concentric tubes called multiwalled nanotubes (MWNT). SWNTs, although predominantly having a single wall, are understood instances within a given sample of tubes having multiple walls in some cases. See, Flauhaut et al., "Synthesis of single-walled carbon nanotube-Co—MgO composite powders and extraction of the nanotubes," J. Mater. Chem. 2000, vol. 10, no 2, pp. 249-252.

The term "MWNT" means a carbon multiwalled nanotube. MWNT's have a near perfect carbon tubule structure that resembles a sheet of $sp^2$ bonded carbon atoms rolled into a seamless tube. They are generally produced by one of three techniques, namely electric arc discharge, laser ablation and chemical vapor deposition. The arc discharge technique involves the generation of an electric arc between two graphite electrodes, one of which is usually filled with a catalyst metal powder (e.g. iron, nickel, cobalt), in a Helium atmosphere. The laser ablation method uses a laser to evaporate a graphite target which is usually filled with a catalyst metal powder too. The arc discharge and laser ablation techniques tend to produce an ensemble of carbonaceous material which contain nanotubes (30-70%), amorphous carbon and carbon particles (usually closed-caged ones). The nanotubes must then be extracted by some form of purification process before being manipulated into place for specific applications. The chemical vapor deposition process utilizes nanoparticles of metal catalyst to react with a hydrocarbon gas at temperatures of 500-900° C. A variant of this is plasma enhanced chemical vapor deposition in which vertically aligned carbon nanotubes can easily be grown. In these chemical vapor deposition processes, the catalyst decomposes the hydrocarbon gas to produce carbon and hydrogen. The carbon dissolves into the particle and precipitates out from its circumference as the carbon nanotube. Thus, the catalyst acts as a 'template' from which the carbon nanotube is formed, and by controlling the catalyst size and reaction time, one can easily tailor the nanotube diameter and length respectively to suit. Carbon tubes, in contrast to a solid carbon filament, will tend to form when the catalyst particle is ~50 nm or less because if a filament of graphitic sheets were to form, it would contain an enormous percentage of 'edge' atoms in the structure. Alternatively, nanotubes may be prepared by catalytic pyrolysis of hydrocarbons as described by Endo, et al., in J. Phys. Chem. Solids, 54, 1841 (1993), or by Terroner, et al., in Nature, 388, 52 (1997) or by Kyotani, et al., in Chem. Mater., 8, 2190 (1996).

MWNTs include double-walled carbon nanotubes (DWNTs). The morphology and properties of DWNTs are similar to SWNTs but their resistance to chemicals is significantly improved. This is especially important when functionalization is required to add new properties to the CNT. In the case of SWNTs, covalent functionalization will break some C=C double bonds, leaving "holes" in the structure on the nanotube and thus modifying both its mechanical and electrical properties. In the case of DWNTs, only the outer wall is modified.

Nanotubes may be functionalized by grafting of chemical functional groups or linking groups at the surface of the nanotubes. In particular, covalent modification schemes allow persistent alteration of the electronic properties of the tubes as well as to chemically tailor their surface properties, whereby new functions can be implemented that cannot otherwise be acquired by pristine nanotubes. Nanotubes may be functionalized, for example, by oxidatively introduced carboxyl, hydroxyl or carbonyl groups or by further addition of ester or amide groups. Bifunctional molecules like diamines may be utilized as linkers. Hydrophilic polymers like polyethylene glycol (PEG) may be used coupled to carboxyl groups. Nanotubes may also be functionalized by direct covalent attachment of functional moieties to the sidewalls. For details, see "Chemically Functionalized Carbon Nanotubes," by Kannan Balasubramanian and Marko Burghard in *Small*, 2005, vol. 1, No. 2, pages 180-192. Embodiments of the invention include nanotubes functionalized with alternating monomer units to form a copolymer.

Nanotubes have been constructed with length-to-diameter ratio of up to 132,000, 000:1, which is significantly larger than any other material. Nanotubes are members of the fullerene structural family, which also includes the spherical buckyballs. The ends of a nanotube might be capped with a hemisphere of the buckyball structure. Their name is derived from their size, since the diameter of a nanotube is on the order of a few nanometers (approximately 1/50,000th of the width of a human hair), while they can be up to 18 centimeters in length. Nanotubes are categorized as single-walled nanotubes (SWNTs) and multi-walled nanotubes (MWNTs).

The nature of the internal bonding of a nanotube is described by applied quantum chemistry, specifically, orbital hybridization. The chemical bonding of nanotubes is composed entirely of sp2 bonds, similar to those of graphite. This bonding structure, which is stronger than the sp3 bonds found in diamonds, provides the molecules with their unique strength. Nanotubes naturally align themselves into "ropes" held together by Van der Waals forces.

The term nanostructure further includes nanotubes, nanofibers and related structures, as described e.g. in "Carbon nanostructures and process for the production of carbon-based nanotubes, nanofibres and nanostructures," US 20070183959.

The term nanostructure further includes boron-carbon materials including nanostructures of boron (B), boron nitride (BN), carbon nitride ($CN_x$), boron-carbon nitride ($B_x C_y N_z$), and boron carbide ($B_x C_y$), where x, y, and z indicate a relative amount of each element compared to the others and where no more than one of x, y, or z are zero for a single stoichiometry. x:y:z may be selected, e.g., from the group consisting of about 1:2:1, about 1:3:0, about 1:0:1, and about 0:1:1. For example, $BC_2N$ or boron-nitride (BN) nanotubes, as described in Zettl, "Non-Carbon Nanotubes," Adv. Mat. 8(5):443-445 (1996). Gold, palladium and platinum nanotubes are also included. See, Yugang et al., "Metal nanostructures with hollow interiors," Advanced Materials, 2003, vol. 15, no 7-8, pp. 641-646. Boron-carbon materials have also been described e.g. in U.S. Pat. No. 6,235,675, which described a method of forming a material containing carbon and boron, and, further, that single crystal boron carbide ($B_4C$) is a high temperature refractory material with a melting temperature in excess of 30 2,400° C. The crystal structure of boron carbide is rhombohedral and consists of 12-atom icosahedral units located at corners of a rhombohedral unit cell connected by C—B—B or C—B—C chains lined along a cell diagonal (O. Chauvet, D. Emin, L. Forro, T. L. Aselage, and Z. Zuppiroli, Phys. 35 Rev. B 53,14450 (1996)).

The term "composite materials", often shortened to composites, means engineered materials made from two or more constituent materials with significantly different physical or chemical properties which remain separate and distinct on a macroscopic level within the finished structure. Composites are made up of individual materials referred to as constituent materials. There are two categories of constituent materials: matrix and reinforcement. At least one portion of each type is required. The matrix material surrounds and supports the reinforcement materials by maintaining their relative positions. The reinforcements impart their special mechanical and physical properties to enhance the matrix properties. A synergism produces material properties unavailable from the individual constituent materials, while the wide variety of matrix and strengthening materials allows the designer of the product or structure to choose an optimum combination. Engineered composite materials must be formed to shape. The matrix material can be introduced to the reinforcement before or after the reinforcement material is placed into the mold cavity or onto the mold surface. The matrix material experiences a melding event, after which the part shape is essentially set. Depending upon the nature of the matrix material, this melding event can occur in various ways such as chemical polymerization or solidification from the melted state.

The term "oligomer" as used herein, and as understood in the art, consists of a few monomer units, e.g. less than 100, or in contrast to a polymer that, at least in principle, consists of an unlimited number of monomers. Dimers, trimers and tetramers are oligomers, and may be referred to as one-two or three-mers of monomer. In certain embodiments, the term "oligomer" will refer to a molecule of 2 subunits, 2-3 subunits, or 2-4, subunits, up to 20 subunits.

The term "crosslinker" is used herein in its conventional sense, i.e. a molecule that can form a three-dimensional network when reacted with the appropriate base monomers.

The term "polyamide" as used herein means a condensation polymer in which more than 50 percent of the groups connecting repeat units are amide groups. Thus "polyamide" may include polyamides, poly(ester-amides) and poly (amide-imides), so long as more than half of the connecting groups are amide groups. In one embodiment at least 70% of the connecting groups are amides, in another embodiment at least 90% of the connecting groups are amides, and in another embodiment all of the connecting groups are amides. The proportion of ester connecting groups can be estimated to a first approximation by the molar amounts of monomers used to make the polyamides.

The term "aromatic polyamide" as used herein means a polyamide in which the monomer units are based on aromatic rings, with functional groups for polymerization. The term "aromatic" means any hydrocarbonaceous compound that contains at least one group of atoms that share an uninterrupted cloud of delocalized electrons, where the number of delocalized electrons in the group of atoms corresponds to a solution to the Huckel rule of 4n+2 (e.g., n=1 for 6 electrons, etc.). Representative examples include, but are not limited to, benzene, biphenyl, naphthalene, and the like. Aromatic polyamides, also used as shortened to "aramid" or "aramid fibers" represent a class of heat-resistant and strong synthetic fibers. They are commercially important polymers used in aerospace and military applications, for ballistic rated body armor fabric and ballistic composites, in bicycle tires, and as an asbestos substitute. They are fibers in which the chain molecules are highly oriented along the fiber axis, so the strength of the chemical bond can be exploited. The Federal Trade Commission definition for aramid fiber is: A manufactured fiber in which the fiber-forming substance is a long-chain synthetic polyamide in which at least 85% of the amide linkages, (—CO—NH—) are attached directly to two aromatic rings.

In para-aramids, all the amide groups are separated by para-phenylene groups, that is, the amide groups attach to the phenyl rings opposite to each other, at carbons 1 and 4. When the aromatic groups are linked into the backbone chain through 1 and 4 positions, it constitutes a para-linkage. An example of a para-aramid structure is given below:

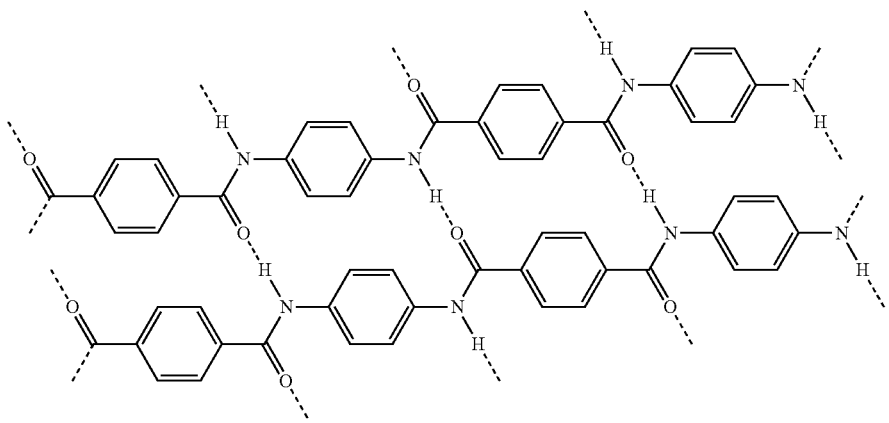

Meta-aramids have meta-phenylene groups, that is, the amide groups are attached to the phenyl ring at the 1 and 3 positions. When the aromatic groups are linked into the backbone chain through 1 and 3 positions, it constitutes a meta-linkage. An example of a meta-aramid structure is shown below, where n is the number of repeating units, typically 100s to thousands:

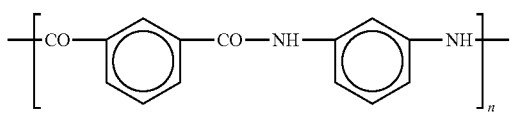

Aramids are generally prepared by the reaction between an amine group and a carboxylic acid halide group. Simple AB homopolymers may look like:

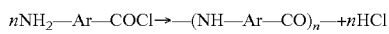

Examples of para-aramids include Kevlar® aramid fiber (Dupont, Wilmington, Del.), and Twaron® aramid fiber (Akzo, Dobbs Ferry, N.Y.). Kevlar® and Twaron® are both p-phenylene terephtalamides (PPTA), the simplest form of the AABB para-polyaramide. PPTA is a product of p-phenylene diamine (PDA) and terephtaloyl chloride (TPC).

Examples of meta-aramids include Nomex® fiber (Dupont, Wilmington, Del.) and Tejinconex® meta-aramid fiber (Teijin, Japan). Nomex® polymer is produced by condensation reaction from the monomers m-phenylenediamine and isophthaloyl chloride.

Examples of polyfunctional amine monomers are aromatic polyfunctional amines such as phenylenediamines in which the two amino groups connected to the benzene have an ortho-, meta- or para-positional relationship, 1,3,5-triaminobenzene, 1,2,4-triaminobenzene, 3,5-diaminobenzoic acid, xylylene diamine, 2,4-diaminotoluene, 2,4-diaminoanisole and amidol, aliphatic amines such as ethylenediamine, propylenediamine and tris(2-aminoethyl)amine, and alicyclic polyfunctional amines such as 1,2-diaminocyclohexane, 1,4-diaminocyclohexane, 1,3-diaminocyclohexane, piperazine, 4-aminomethylpiperazine and 2,5-dimethylpiperazine. Of these, from the point of view of ready availability and ease of handling, and from the point of view of the properties of the composite semipermeable membrane obtained, the use of m-phenylenediamine (hereinafter referred to as m-PDA), p-phenylenediamine, 1,3,5-triaminobenzene, ethylenediamine and piperazine is preferred. These amines can be used on their own, or they may be used as mixtures. For a further description, see U.S. Pat. No. 6,521,130.

Examples of monomers that may be used in the mixtures in combination with the above-mentioned polyfunctional amine monomers are diacyl chlorides, such as terephthaloyl chloride (TPC), isophthaloyl chloride, difluorobenzoquinone, dichlorodiphenylsulfone, Overview Described below are methods for sequential functionalization of nanotubes and other nanostructures by covalent modification of the nanotube with a linking group which allows attachment of repeat units of a polymer, preferably a ultra-high-strength polymer. This step-by-step functionalization procedure represents a systematic methodology whereby a novel hybrid material is created which possesses chemical functionality identical to the ultra-high strength polymer. It is postulated that such oligomers at the surface of the nanotubes facilitate interaction with a host polymer matrix via terminal functional groups and also via the tangential hydrogen bonding interactions and pi-pi interactions on account of the polymer functionality. To test this hypothesis, polymer-MWNT/polymer and pristine-MWNTs/polymer composites were prepared and characterized.

The present oligomer-nanostructure composites are preferred for use in structural materials, i.e. those that take advantage of the strength and/or thermal properties of the included nanostructures (e.g. MWNT). However, they can be used to impregnate or coat substrates, including, but not limited to, the following substrates: woven glass, non-woven glass, copper (a resin coated copper), quartz fabric reinforcement, cross plies of unidirectional tape, film, fibre, or paper (woven or non-woven) derived from polyester LCP such as Vectra® polymer (Hoechst-Celanese, Bridgewater, N.J.) based on hydroxynapthoic acid and hydroxybenzoic acid; polyimide film including Kapton® film (Dupont, Wilmington, Del.), Upilex (UBE Industries, Tokyo Japan) based on biphenyltetracarboxylicdianhydride and either of p-phenylenediamine (PDA) or 4,4'-diaminodiphenylether, Thurmount® polymer (Dupont, Id.); polyaramides such as Teijin's Technora® polymer (Teijin America, Inc. New York, N.Y.) based on PDA and 3,4'-diaminodiphenylether, meta-aramids such as Nomex® polymer (Dupont, Id.) based on poly(m-phenyleneisophthalamide), and Teijinconex® polymer, para-aramids including Kevlar® fiber and Twaron® fiber (Akzo, Dobbs Ferry, N.Y.) based on poly(p-phenyleneterephthalamide) and polybenzoxazole.

Covalent attachment of oligomers to the surface of nanotubes results in oligomer units forming an organic sheath around the nanotubes, polymer-functionalized-nanotubes (P-NTs). P-NTs possess chemical functionality identical to that of polymer, and thus provide nanoscale scaffolds which may be readily dispersed within a monomer solution and participate in the polymerization reaction to form a polymer-NT/polymer composite. We show that formation of polymer in the presence of P-NTs leads to a uniform dispersion of nanotubes within the polymer matrix, in contrast to aggregated masses of nanotubes in the case of pristine-MWNTs. The covalent attachment of oligomeric units to the surface of nanotubes represents the formation of a functional nanoscale building block which can be readily dispersed and integrated within the polymer to form a novel composite material. The implications of tuning the surface chemistries of carbon nanotubes (CNTs) to the chemistry of host polymer matrices are considered.

Nanostructures

The starting materials are preferably carbon nanotubes, more preferably multi-walled nanotubes (MWNTs). In one embodiment, nanotubes have been functionalized sequentially with monomer units of a polymer to yield polymer-functionalized-MWNTs, allowing for not just a physical mixture of nanotubes and polymer, but a structurally and chemically multicomponent system suitable for next-generation composites.

Generally, attachment of the monomers requires an initial modification of the surface of the nanostructure. The nanostructure will have an essentially pristine outer layer, as shown by way of example below:

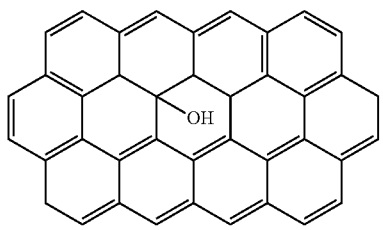

A few defects will exist, as illustrated by the hydroxyl group. In the present process, the surface of the nanostructure is treated to attach a number of functional groups on the surface as illustrated below:

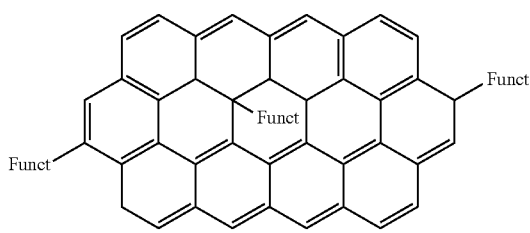

The functional groups are shown on the edges of the material for clarity, but in practice will involve breaking atomic bonds within an outer surface sheet of the nanostructure. In fact, the nanostructure may be a continuous rolled tube of graphene sheet (MWNT, DWNT or SWNT). The chemical nature of the functional groups ("Funct") will be chosen depending on the application and desired process steps. Exemplified below is treatment with an oxidative acid, followed by conversion of the acid groups to acid chloride, facilitating amide linkage, as illustrated in FIG. 1. However, other surface treatments of the nanostructure may be used, as described below.

As described in Bianco et al., US 2008/0008760, one can prepare carbon nanotubes with substituted pyrrolidine rings on n the surface, which provide linking groups for the methods taught here.

When using carbon nanostructures, it is preferred that the structures are of extended length, and are not intentionally shortened. The nanostructures, e.g. MWNT having 3-50 walls, or DWNT may be doped with other atoms to provide additional atomic sites for linkage. Specific examples of the dopant substances include any one kind or a mixture of the like of at least two kinds of various carbon clusters such as fullerenes and super fullerenes and metal encapsulating fullerenes comprising metals encapsulated therein; various metals such as alkali metals and transition metals; organic compounds such as aromatic compounds; organometallic compounds represented by ferrocenes; organic metal complexes and inorganic metal complexes; and inorganic solid compounds. Further details are given in Ijima et al., "Method for manufacturing hybrid carbon nanotube," U.S. Pat. No. 7,384,520.

In some embodiments, boron nitride nanotubes (BNNTs) are used instead of carbon nanotubes. BNNTs can be synthesized on Si substrates by thermal decomposition of B and MgO powders in an ammonia environment at 1200.degree.C. in an electric furnace. US 2010/0051879 by Sainsbury; et al., published Mar. 4, 2010, entitled "Functionalized Boron Nitride Nanotubes," describes a plasma treatment used to modify the surface of BNNTs. In one example, the surface of the BNNT has been modified using ammonia plasma to include amine functional groups derived from nitrogen in the BNNT. Once amine functional groups are attached to BNNTs, other species can be attached to the amine groups. In an exemplary embodiment, amine functional groups attached to BNNTs were used to couple short chain organic molecules terminated with a thiol, 3-mercaptopropionic acid (MPA), to the surfaces of the BNNTs via standard diimide-mediated amide formation. The present boron nitride nanotubes may also be boron carbon nitride nanotubes of various formulas indicated by BxCyNz, where x, y, and z indicate a relative amount of each element compared to the others and where no more than one of x, y, or z are zero for a single stoichiometry. A full description of such nanotubes is contained in US 2001/0023021, incorporated by reference, as are all other references cited herein.

Functionalization of the Nanostructures

It is important that a high degree of functionalization of the nanostructure be obtained in order to couple a large number of oligomers on the surface of the nanostructure. The present nanostructures are functionalized to produce a high density of surface bound functional groups, in that at least about 0.5% or about 1% of the lattice atoms are functionalized. In some cases, 1-2% of the lattice atoms may be functionalized, or 3-5% of the lattice atoms may be functionalized, even up to 20% of the lattice atoms may be functionalized. The lattice atoms may be carbon atoms in a graphene pattern on the surface of a nanotube (DWNT, MWNT or SWNT), nitrogen atoms in a BCN nanotube, etc. The level of functionalization is controlled by controlling conditions of the reaction, such as oxidation.

As described, e.g. in Haddon et al., U.S. Pat. No. 6,368,569, one may carry out a process involving reacting CNTs with a mineral acid. This may be accomplished by adding a mineral acid (eg. HCl, HNO3, H2SO4) to an aqueous suspension of the CNTs to protonate the carboxylate groups. The attaching step includes directly reacting the carbon nanotubes with an amine having a formula RNH2 or R^NH wherein R, R± and R2=(CH2)nCH3 where n=9-50. Alternatively, the attaching step includes directly reacting the carbon nanotubes with an alkylaryl amine having a formula RNH2 or RjR2NH wherein R, R± and R2=(C6H4)(CH2)^CH3 where n=5-50.

As described in Park et al., "Covalent Modification of Multiwalled Carbon Nanotubes with Imidazolium-Based Ionic Liquids: Effect of Anions on Solubility," *Chem. Mater.*, 2006, 18 (6), pp 1546-1551, multiwalled carbon nanotubes (MWCNTs) were covalently modified with imidazolium salt-based ionic liquids (ILs). Coupling of acid chloride-functionalized MWCNTs with commercially available (3-aminopropyl)imidazole, followed by the reaction with n-butyl bromide, afforded 1-butylimidazolium bromide salt-functionalized MWCNTs.

It is important that the functionalization of the outer wall be carried out in a selective and controlled manner. Oxidation is preferred. Oxidation with strong oxidizing agents in a scalable process is preferred, use of oxidizing acids such as nitric, sulfuric or mixtures thereof are also preferred.

In accordance with another alternative, the attaching step includes the steps of (a) converting the carboxylic acid groups on the carbon nanotubes to acid chloride groups by reacting the carbon nanotubes with a reagent selected from a group consisting of SOC12, PC15 and any mixtures thereof; (b) mixing the acid chloride converted carbon nanotubes with an amine or alkylaryl amine having a formula RNH2 or R^NH wherein R, R± and R2=(CH2)^CH3 and n=9-50 or R, R1 and R2=(C6H4)(CH2)nCH3 and =5-50; and (c) heating the resulting mixture to a temperature between 50-200° C. More preferably, the heating step is to 90-100° C. for at least 96 hours.

In another embodiment, MWNTs are covalently functionalized by attaching alternating monomer units to result in nanotubes surface-functionalized with up to 1-4 repeat units of a polymer, thus oligomer-functionalized MWNTs.

In another embodiment, nanotubes are specifically functionalized to adopt the chemical properties identical to those of the polymer and, furthermore, to allow surface bound reactive chemical groups to facilitate the nature of the interaction between tubes and matrix or substrate. In particular, MWNTs functionalized specifically with chemistries identical to their intended host matrix of a composite are disclosed.

Single-walled or multi-walled carbon nanotubes are functionalized by derivatizing one or more organic functional groups. Nanotubes can be functionalized by any of the organic functional groups which are disclosed in Khabasheshku, et al (U.S. Pat. No. 7,125,533). In one example, nanotubes are functionalized by adding concentrated acid to yield carboxylic acid-functionalized nanotubes. In another example, carboxylic acid-functionalized-nanotubes can be further converted to acid-chloride-functionalized nanotubes.

Choice of Polymer

Organic-group-functionalized-nanotubes are reacted with one or more monomers of a polymer in which one or more monomer units are sequentially added to the functionalized nanotubes.

One class of polymer which has commercial significance for the preparation of ultra-high strength materials is polyaramids. Most notably, the poly-aramid poly-p-phenylene terephthalamide (PPTA), e.g., Kevlar® aramid fiber, has attracted interest in recent years concerning its integration with carbon nanotubes due to the extreme physical properties of both materials. Recent reports have described the physical combination of these materials to form composites.[21,22] Unfortunately, such primitive physical mixing, although simple, has its drawbacks. It is well known that basic physical integration of nanotubes and polymers allows formation of aggregates which act as defect sites within polymers and may result in slippage between the materials. Highly desirable would therefore be the ability to structurally and chemically integrate and bind materials such as Kevlar® aramid fiber and nanotubes together. The synthesis of PPTA resulting from the polycondensation of terephthaloyl chloride (TPC) and p-phenylenediamine (PDA) has been an established procedure since the early 1960's.[23] In some embodiments, multi-walled carbon nanotubes (MWNTs) are covalently functionalized by attaching alternating monomer units PDA and TPC to result in nanotubes surface functionalized with one and a half repeat units of the polymer PPTA, thus PPTA-oligomer-functionalized-MWNTs.

Embodiments of the present invention also include the meta-variants of the polyaramids, e.g., the polymer polymetaphenylene isophtalamide (MPIA) as exemplified by Nomex® fiber. In some embodiments, nanotubes are covalently functionalized by attaching alternating monomers m-phenylenediamine and isophthaloyl chloride to result in nanotubes functionalized by repeat units of the polymer polymetaphenylene isophthalamide (MPIA).

Other embodiments include using polymers such as polyester LCP based on hydroxynapthoic acid and hydroxybenzoic acid; polyimide film based on biphenyltetracarboxylic-dianhydride and either of p-phenylenediamine (PDA) or 4,4'-diaminodiphenylether; polyaramides based on PDA and 3,4'-diaminodiphenylether, meta-aramids based on poly(m-phenyleneisophthalamide), and para-aramids based on poly (p-phenyleneterephthalamide) and polybenzoxazole.

In another embodiment, polymer is prepared using methods known in prior art in the presence of polymer-nanotubes to yield polymer-nanotubes/polymer composites. The resultant composite typically shows polymer-nanotubes dispersed throughout the polymer matrix due to the extensive functionalization of the surface of nanotubes with oligomers. This dispersion is in contrast to the aggregation seen when pristine nanotubes are used instead of polymer-nanotubes.

A variety of oligomers may be attached to the nanostructures and used in composites where the oligomers are extended to polymers and a compatible (or identical) polymer is used as a matrix for the nanostructure-linked polymers. The matrix polymer may be present in a predetermined ration with the nanostructure-lined polymers, e.g. where the nanostructure-lined material is about 0.5-1%, 1-10%, 10-20%, or even up to 99% of the total weight of the material.

Exemplified below is a copolymer of PDA and TPC, where monomers alternate. Other aromatic polyamides, including meta-aramids may be used.

In addition, polymers may be chosen that form composites utilizing the unique thermal electrical or optical properties of the nanostructure used. For example, carbon nanostructures such as MWNTs may be combined with photovoltaic polymers in a solar cell configuration. The photovoltaic material is preferably a polymer, such as P3HT, PEDOT, MDMO-PV, or PFTBT. Also preferably, the polymer is hole-conducting, such that electrons and holes are spatially separated in the device. Examples of suitable polymers, as well as methods of making such polymers can be found, e.g., in "Polymer based photovoltaics: Novel concepts, materials, and state-of-the art efficiencies", by Kroon et al, published in the proceedings of the European Photovoltaic Solar Energy Conference and Exhibition, 2005.

Poly (e-hexylthiophene), P3HT, is useful in that incident light is absorbed mainly over the wavelength range of 450 nm to 600 nm. Another organic material that may be employed is 3,4,9,10-perylenetetracarboxylic-bis-benzimidazole (PTCBI). The actual thickness of the organic polymer absorber must generally be very thin, on the order of about 100 to 150 nm. One may also use polymers based on copper iodine chains. By using a co-crystal scaffolding, poly(di-iododiacetylene), or PIDA, can be prepared as a nearly unadorned carbon chain substituted with only single-atom iodine side groups. The monomer, diiodobutadiyne, forms co-crystals with bis(nitrile) oxalamides, aligned by hydrogen bonds between oxalamide groups and weak Lewis acid-base interactions between nitriles and iodoalkynes. In co-crystals with one oxalamide host, the diyne undergoes spontaneous topochemical polymerization to form PIDA. Further details are set forth in Sun et al., "Preparation of poly(diiododiacetylene), an ordered conjugated polymer of carbon and iodine," Science, 2006 May 19; 312(5776):1030-4. This application may use nanostructures such as fullerenes such as C60, functionalized $C_{60}$, such as $C_{60}$-PCBM, single wall nanotubes; nanotubes such as carbon single walled and multi wall nanotubes, nanowires, and quantum dots.

EXAMPLES

Experimental Section

MWNTs used in this study were arc-discharge produced, and were supplied by MER Corporation, Tucson, Ariz., USA. Terephthaloyl chloride was purchased from Fluka and was purified by exposure to thionyl chloride and recrystallized from hexanes prior to use. N-methylpyrrolidinone (NMP) purum., absolute, over molecular sieves (H2O≤0.01%), ≥98% (GC) was purchased from Sigma Aldrich and was purified by vacuum distillation after drying over calcium hydride. Water (dd-$H_2O$) used for purification of oxidized MWNTs was deionized using a NANOpure™ purification system (Barnstead, USA). FT-IR spectra were recorded with a Nicolet 6700 using a Smart Orbit™ ATR accessory (Si Crystal). Raman spectra were recorded with a Renishaw in Via Raman Microscope using 633 nm and 534.5 nm excitation sources. Scanning Electron Microscopy (SEM) was conducted with a FEI Sirion XL30 Scanning Electron Microscope (SEM). Palladium metal was evaporated onto composite samples to a thickness of approximately 10-15 nm to assist in the imaging of non-conductive regions by SEM. Samples for SEM analysis were prepared by dispersion of composite material in $CH_2Cl_2$ and the evaporation of a drop onto a piece of silicon wafer substrate. Transmission Electron Microscopy (TEM) was conducted with a JEOL 2010 Transmission Electron Microscope. Preparation of samples for TEM involved the deposition of a drop of nanotube dispersion (DMF) onto a 2000 square mesh copper TEM grid, followed by several drops of to allowing wicking of the solvent and evaporation to dryness. Sonication was conducted using a Cole-Palmer Ultrasonic Bath 8890. All other chemicals and reagents were purchased from Sigma Aldrich and used as received. Schlenk apparatus used in this work was operated in conjunction with dry $N_2$, at $4\times10^{-3}$ Torr.
Preparation of PPTA-Functionalized MWNTs Briefly, PPTA-functionalized-MWNTs were prepared via the covalent attachment of PDA molecules to acid chloride functional groups at the surface of the MWNTs. Acid chloride functionalized MWNTs were prepared by the introduction of carboxylic acid functional groups at the surface of the MWNTs using established strong acid oxidative treatment[24-28] and the subsequent conversion of the acid groups to acid chloride groups.[29] PDA monomer units were covalently bound to the acid chloride-MWNTs via amide formation. This was followed by a further covalent coupling of TPC monomer units and a final PDA coupling to the TPC groups to yield one and a half repeat units of PPTA at the surface of the MWNTs in a PDA-TPC-PDA-MWNTs configuration, thus PPTA-MWNTs.
Preparation of Carboxylic Acid Functionalized-MWNTs (COOH-MWNTs)

MWNTs (0.5 g) were added to concentrated nitric acid (70%, 500 mL) and sonicated for 15 mins to ensure adequate dispersion of the material. The nanotube suspension was refluxed at 130° C. for 24 h. The suspension of MWNTs was allowed cool and was then filtered using a membrane filtration apparatus (Kimble, 90 mm) in conjunction with a Teflon™ filter (Millipore, Omnipore™, 0.2 μm), and washed thoroughly with water (DI)(3 L). The MWNTs were then dispersed into water (DI)(500 mL), to which $KMnO_4$ (1.50 g, $9.50\times10^{-3}$ mol) was added under vigorous stirring. The suspension was cooled to 5° C., and was acidified by the dropwise addition of $HClO_4$ (70%, 500 mL). Cooling was removed and the suspension allowed reach room temperature. An excess of citric acid-monohydrate (31 g, 0.148 mol) was added to the stirring suspension in order to quench the $KMnO_4$, this was evidenced by the colour change of the suspension from a dark purple to a clear suspension of the MWNTs. The MWNTs were filtered as before, and washed thoroughly with water (DI)(10 L).
Preparation of Acid-Chloride Functionalized-MWNTs (COCl-MWNTs)

COOH-MWNTs (0.100 g) were dried using a Schlenk line (24 h). Thionyl Chloride (200 mL, 2.74 mol) was added to the dry COOH-MWNTs and sonicated (15 min) to allow complete dispersion of the COOH-MWNTs in the $SOCl_2$. The suspension was heated to 70° C. under $N_2$ with magnetic stirring for 24 h to allow conversion of the carboxylic acid to acid chloride groups. $SOCl_2$ and associated by-products were removed by rotary evaporation followed by Schlenk drying (6 h).
Preparation of P-Phenylenediamine-Functionalized-MWNTs (PDA-MWNTs)

A solution of p-phenylenediamine (PDA) (0.50 g, $4.62\times10^{-3}$ mol) in NMP(anhydrous) (200 mL) was added to COCl-MWNTs (0.100 g), prepared as described above. The solution was sonicated (15 min) to allow the complete dispersion of COCl-MWNTs in the PDA solution. The suspension was heated to 50° C. to promote optimum dispersion and exfoliation of the COCl-MWNTs within the solution and to promote the coupling of PDA at the surface of the COCl-MWNTs via amide formation. The appearance of the suspended material at this stage resembled a rich black oil-like material, giving preliminary indication to a favourable dispersion and reaction of the COCl-MWNTs in the suspension. The suspension was allowed stir for 12 h, throughout which intermittent sonication (5 min at 2 h intervals) was performed in order to ensure optimum dispersion of materials. PDA-MWNTs were then recovered by filtration (as described above) and were washed thoroughly with NMP (500 mL), ethanol (500 mL) and methanol (500 mL) to ensure complete removal of excess PDA.

Modification of PDA-MWNTs with Terephthaloyl Chloride (TPC) to Form TPC-PDA-MWNTs A solution of TPC (0.938 g, 4.62×10$^{-3}$ mol) in NMP (anhydrous) was added to PDA-MWNTs (0.100 g) which had been dried using a Schlenk line (6 h). The PDA-MWNTs were sonicated (15 mins) into suspension, and the material heated to 50° C. under magnetic stirring for 12 h to facilitate the covalent coupling of TPC to PDA-amino groups at the surface of the PDA-MWNTs (intermittent sonication, 5 min, every 2 h). The physical appearance of the suspension remained consistent with the previous step, i.e. a rich black suspension resembling an oil-like substance. The TPC-PDA-MWNT material was filtered (as described above) and was thoroughly washed with NMP(anhydrous) (1.5 L) to allow removal of un-reacted TPC. The TPC-PDA-MWNTs were immediately transferred to a round-bottomed flask by sonicating the material off the Teflon™ filter membrane using NMP (30 mL).

Modification of TPC-PDA-MWNTs with PDA to Form PDA-TPC-PDA-MWNTs

A solution of PDA (0.50 g, 4.62×10$^{-3}$ mol) in NMP(anhydrous) (200 mL) was added to TPC-PDA-MWNTs (0.100 g), prepared as described above. The material was sonicated (10 min) to ensure adequate dispersion of the MWNTs and resembled a rich black suspension as before. The suspension was heated to 50° C. and allowed to stir for 12 h, with intermittent sonication (5 min, every 2 h). The PDA-TPC-PDA-MWNTs were filtered and washed with NMP (500 mL), ethanol (500 mL) and methanol (500 mL) to ensure complete removal of excess PDA. As material which has been allow to form a cake on top of a filter membrane has the potential to trap un-reacted materials, the material was re-dispersed in methanol (1 L) and filtered once more followed by washing with methanol (1 L). PDA-TPC-PDA-MWNTs were recovered from the filter and dried on a Schlenk line (6 h) before use.

Preparation of PPTA/MWNT and PPTA/PPTA-MWNTs Composites

The polycondensation between TPC and PDA to form PPTA, was based on published experimental details and was carried out in the presence of MWNTs to result in 1 wt % MWNT-impregnated PPTA composites.[23,30] For comparative purposes, composites of PPTA with pristine as-received MWNTs (p-MWNTs), denoted PPTA/p-MWNTs, and PPTA with PDA-TPC-PDA-MWNTs (PPTA-MWNTs), denoted PPTA/PPTA-MWNTs were prepared. Briefly; p-phenylenediamine (PDA) (5.28 g, 4.88×10$^{-2}$ mol) was dissolved in NMP (50 mL), and the solution cooled to 3° C. under magnetic stirring. MWNTs (either p-MWNTs or PPTA-MWNTs, 0.100 g) were added to the stirring solution and sonicated (10 min) to ensure dispersion of the material. A solution of TPC (9.92 g, 4.88×10$^{-2}$ mol) in NMP was added to the stirring MWNTs/PDA solution. This resulted in the immediate formation of the polymer PPTA, evidenced by the formation of a paste-like opaque yellow-green material. The material was filtered using membrane filtration equipment, and was washed by NMP (500 mL) and methanol (500 mL) to ensure removal of the reaction by-product, HCl. The resultant material was vacuum dried using Schlenk apparatus (6 h) and yielded ca. ~10.2 g of MWNT-impregnated-PPTA.

Preparation of PPTA-Functionalized-MWNT

Figure 2:
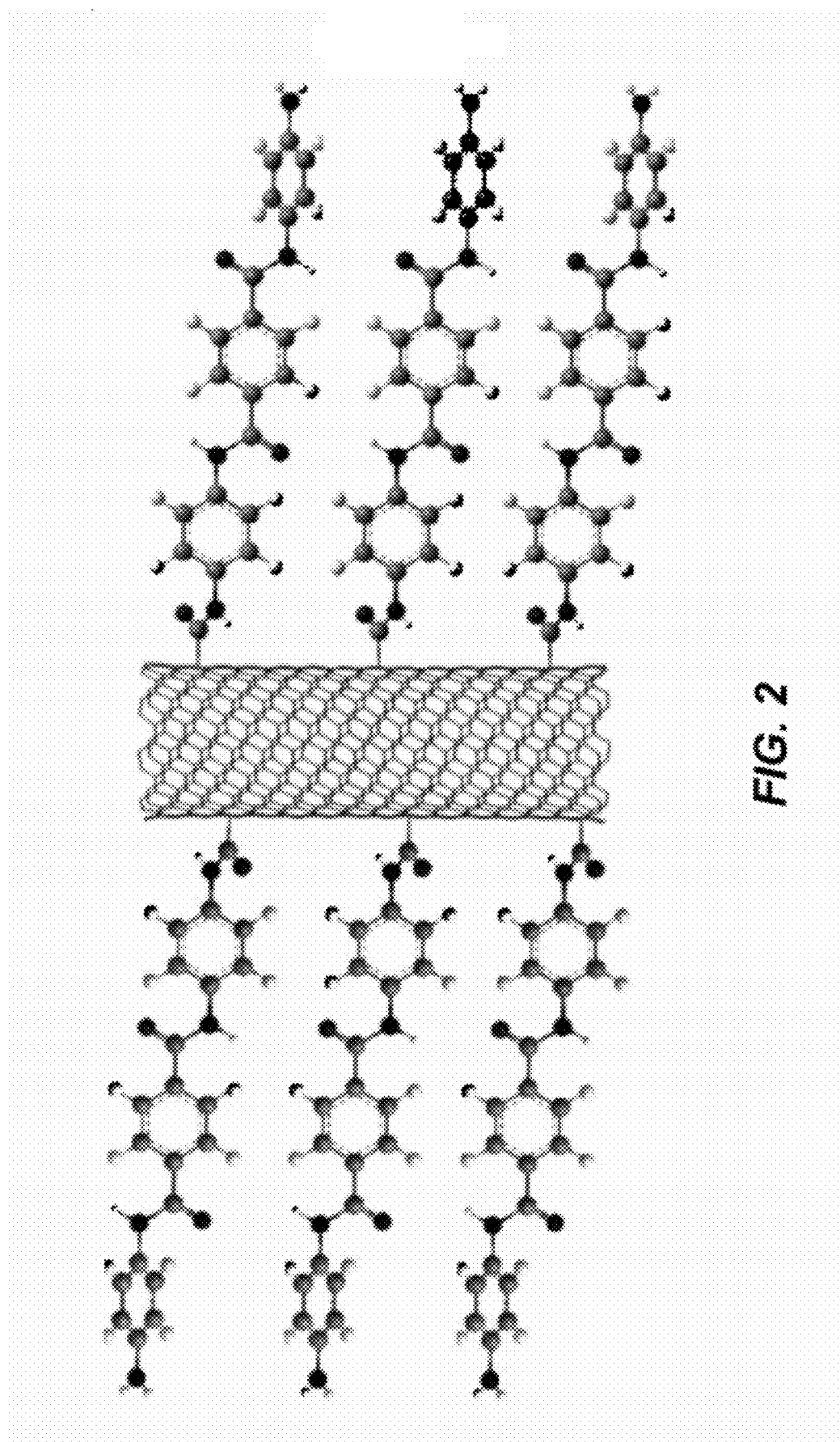
FIG. 2 is a structural representation of PPTA-functionalized MWNTs.

The preparation of PPTA-functionalized-MWNTs was achieved by the sequential covalent attachment of PPTA monomers, PDA and TPC to the surface of acid chloride-functionalized-MWNTs, as depicted in FIG. 1. Following oxidative treatment, carboxy-functionalized-MWNTs (COOH-MWNTs) were converted to the corresponding acid chloride-MWNTs (COCl-MWNTs) to allow efficient, catalyst-free, amide formation in organic solvents.[29] PDA was coupled to the surface of the COCl-MWNTs via amide formation to yield PDA-MWNTs, as shown in FIG. 1a. Subsequent coupling of TPC to PDA-MWNTs using identical methodology was performed to yield TPC-PDA-MWNTs, FIG. 1b. Finally, PDA was coupled to acid chloride groups at the terminal positions of the TPC-PDA-MWNTs to yield PDA-TPC-PDA-MWNTs, FIG. 1c. Thus, PDA-TPC-PDA-MWNTs, hereafter referred to in general terms as PPTA-MWNTs, represent a hybrid material of PPTA oligomer units covalently bound to the surface of the MWNTs. A structural model of the composite is represented in FIG. 2.

The oxidation of MWNTs to introduce surface bound functional groups using strong acid can be done according to published methods.[24-28] This solution based oxidative procedure with MWNTs is particularly attractive as it is readily scalable and results in reproducible surface functionalization of nanotubes. Contrary to popular belief, this procedure can be tuned to yield negligible damage to the nanotubes, by using carefully controlled reaction conditions together with an appropriate choice of nanotube. Indeed, typical commercial arc-grown MWNTs such as those used in this study commonly have over 20 walls so that even if harsh oxidative treatment were to alter the structure of an outer wall, the effect on the total MWNT integrity is negligible.

In view of this, we employed strong acid oxidation treatment which is known to introduce carboxy, hydroxyl and carbonyl groups at the surface of MWNTs in the approximate ratio 4:2:1 respectively.[27] Consequently, we also performed a second oxidative treatment using acidified potassium permanganate in order to oxidize hydroxyl and carbonyl groups to carboxylic acid which can be employed for covalent coupling chemistry.[28]. The structural integrity of the MWNTs was characterized using TEM following acid oxidation and was found to remain intact. TEM of MWNTs following the oxidative treatment shows that the overall structural integrity of the nanotubes is intact. The overall multi-walled structure of the nanotubes was unaffected by the acid oxidation. It is speculated that only several outer-most walls may become substantially oxidized at defect sites, dislocations and regions of strain in the nanotube lattice. From the TEM imaging it is clearly seen that underlying walls appear completely unaffected, and thus importantly retain the intrinsic mechanical properties of the nanotube.

Raman Spectroscopy of MWNTs

Figure 3A:
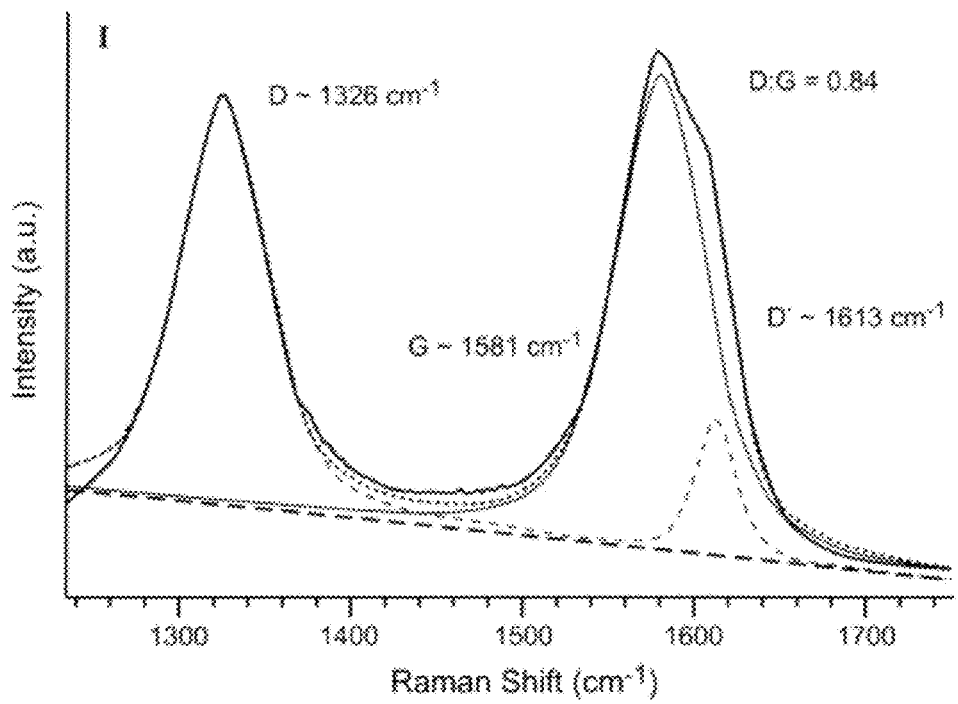
FIG. 3a-b shows Raman spectra of 3a) pristine-MWNTs and 3b) PDA-TPC-PDA-MWNTs.
Figure 3B:
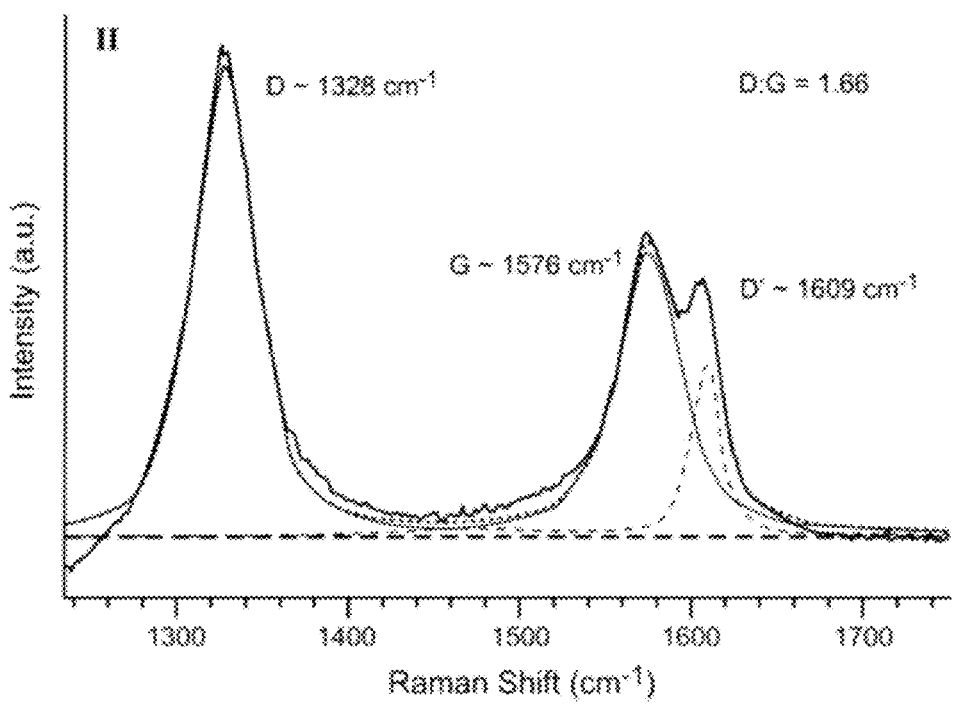
Figure 4A:
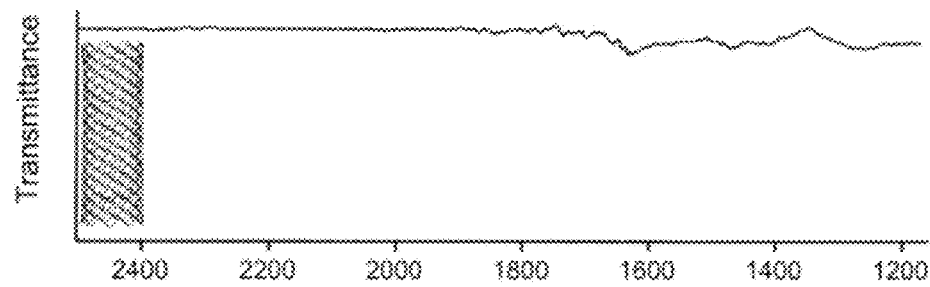
FIG. 4a-d shows FT-IR Spectra of 4a) pristine-MWNTs, 4b) PDA-MWNTs, 4c) TPC-PDA-MWNTs and 4d) PDA-TPC-PDA-MWNTs following sequential functionalization by p-phenylenediamine (PDA) and terephthaloyl chloride (TPC) units.
Figure 4B:
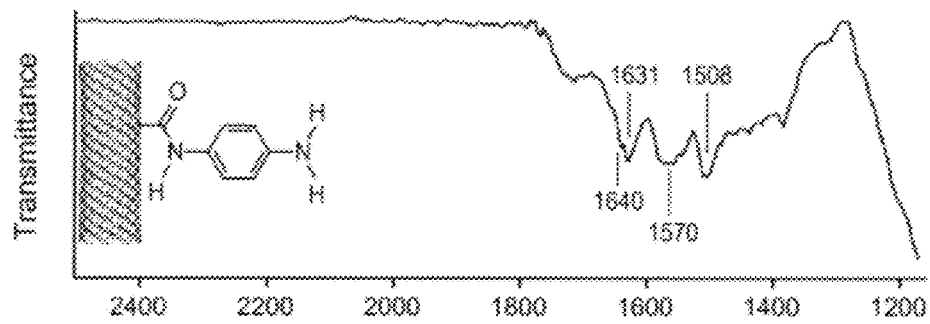
Figure 4C:
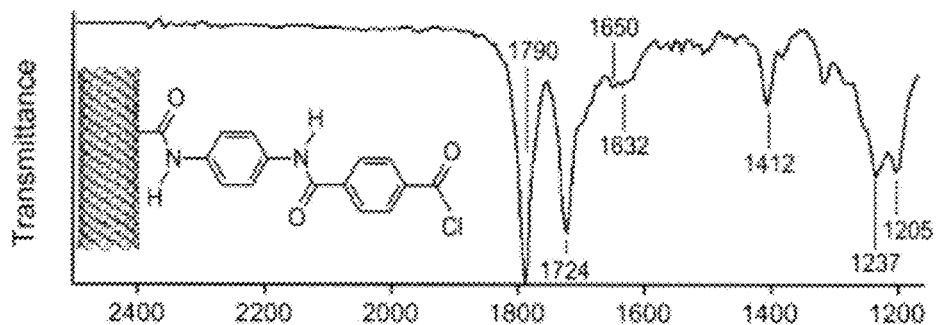
Figure 4D:
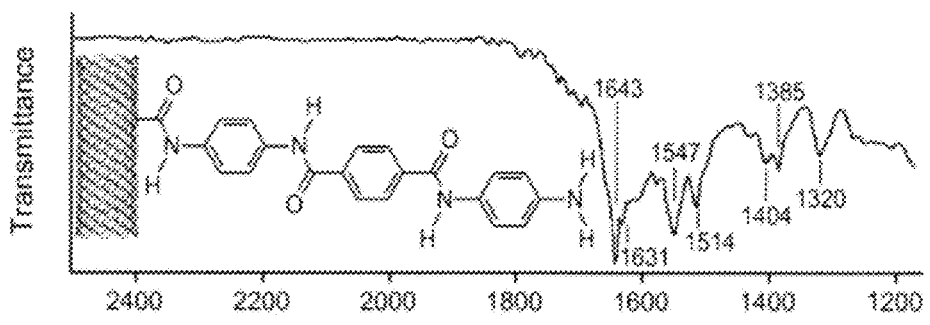

Raman spectroscopy of both pristine-MWNTs (p-MWNTs) and carboxy-MWNTs (COOH-MWNTs) indicated a significant difference between the MWNTs λ=633 nm). The spectrum of p-MWNTs shows a characteristic tangential-mode G peak at 1581 cm$^{-1}$, a D' shoulder at 1613 cm$^{-1}$, and a disorder D peak at 1326 cm$^{-1}$ (FIG. 3a). The spectrum of the COOH-MWNTs shows the tangential mode G peak, now at 1576 cm$^{-1}$ has significantly decreased in intensity relative to the disorder peak D at 1328 cm$^{-1}$ (FIG. 3b). The D' peak at 1609 cm$^{-1}$ has increased in intensity, which is known to indicate disorder in nanotubes,[29] and is comparable in size to the G peak. The $I_D/I_G$ ratio increases upon functionalization from 0.84 to 1.66 indicating an extensive increase in the number of defects in the nanotubes. Such changes are of course fully expected. It is particularly gratifying that spectroscopic evidence together with the TEM data indicates beneficial modification of the MWNTs surface following oxidation, and that, despite this, the nanotube core remains structurally intact.

Characterization of Functionalized MWNTs by FT-IR

The functionalization of COCl-MWNTs with PDA and TPC molecules was characterized by FT-IR spectroscopy (FIG. 4). Relative to the comparatively featureless spectrum of pristine MWNTs (p-MWNTs) (FIG. 4a), the spectrum of PDA-MWNTs exhibits clear indication of the covalent coupling of PDA molecules to the surface bound acid chloride groups of the COCL-MWNTs (FIG. 4b). The appearance of a broad band centred at 1631 cm$^{-1}$ with a distinctive shoulder at 1640 cm$^{-1}$ is believed to be a combination of the N—H bend of the free amino group coupled with the amide I C=O absorption. A broad band centred at 1570 cm$^{-1}$ is attributed to the amide II N—H absorption, while the band at 1508 cm$^{-1}$ indicates the C=C absorption of the aromatic ring. The appearance of these bands and the fact that N—H bands are present due to both amine and amide groups give firm evidence for the covalent attachment of PDA molecules at the surface of the MWNTs. Following subsequent coupling of TPC to PDA terminal amino groups via amide formation, TPC-MWNTs were characterized. The appearance of intense bands at 1790 cm$^{-1}$ and 1724 cm$^{-1}$ are indicative of the C=O of an acid chloride in both free and hydrogen bound states (FIG. 4c). Bands at 1650 cm$^{-1}$ and 1632 cm$^{-1}$ are due to the amide I C=O stretch and the amide II N—H bend respectively. The aromatic C=C stretching band is found at 1412 cm$^{-1}$, while two equivalent bands at 1237 cm$^{-1}$ and 1205 cm$^{-1}$ are indicative of the two forms of p-di-substituted benzene rings which collectively support the assertion of the covalent modification of PDA-MWNTs with TPC to form TPC-PDA-MWNTs.

Further coupling of PDA to the terminal acid chloride groups of the TPC-PDA-MWNTs was performed. In contrast to the spectrum of the TPC-PDA-MWNTs (FIG. 4c) where the C=O stretch of the acid chloride groups appear as intense bands, in the case of PDA-TPC-PDA-MWNTs (FIG. 4d), these bands are absent and have been replaced by the sharp amide I C=O absorption at 1643 cm$^{-1}$ with a shoulder at 1631 cm$^{-1}$ of the amide II N—H absorption. The N—H bend of the terminal amino group of the PDA molecule is seem at 1547 cm$^{-1}$ while the sharp absorption of the aromatic C=C stretching is seen at 1514 cm$^{-1}$. Bands at 1404 cm$^{-1}$ and 1385 cm$^{-1}$ are due to the aromatic C—H bend, while a band at 1320 cm$^{-1}$ is due to the phenyl C—N stretch. Notably, the amide I band has increased in intensity as might be expected due to both the presence of additional amide functional groups and due to the increased vibrational freedom of molecules subsequently bound to the surface of MWNTs. This effect is well known in the case of ligands bound to the substrates and nanoparticles, where groups α to the surface are often weak or indistinguishable, while ω groups are typically well defined.[32] Thus, the combined FT-IR spectroscopic evidence supports the assertion that the covalent step-by-step functionalization of MWNTs with PDA and TPC units had been successful.

Integration of Functionalized MWNTs within Host Polymer Matrix

HR-TEM was used to image the surface of the PDA-TPC-PDA-MWNTs following functionalization and shows a significant amount of organic material at the surface of the MWNTs (FIG. 5). This feature is encouraging as it indicates that the surface of the MWNTs has been extensively functionalized at defect sites to yield a dense monolayer of PPTA oligomers. Such a high degree of surface functionalization is expected to be optimal for the potential integration of functionalized MWNTs within a host polymer matrix such as PPTA, Kevlar.

To test this hypothesis, poly-p-phenylene terephthalamide (PPTA), Kevlar, was prepared using a procedure based on literature preparative methods in the presence of both p-MWNTs and PPTA-MWNTs.[30] As the PPTA-MWNTs possess surface chemistry identical to that of the PPTA host matrix, it was expected that the PPTA-MWNTs would be integrated within the PPTA. Alternatively, p-MWNTs, possessing little or no surface functionality, might be expected to aggregate amongst themselves and form insoluble nanotube regions within the PPTA matrix. Such behaviour of MWNTs within polymer matrices is extremely common and has been the underpinning motivation for a multitude of nanotube-polymer composite studies aimed at preventing such behaviour. In this case, 1 wt % MWNT-PPTA composites were prepared by forming PPTA in the presence of p-MWNTs and PPTA-MWNTs. Optical images of the composites indicated distinct differences between the materials (FIG. 6a,b). PPTA is opaque yellow in colour, while the composites of p-MWNTs/PPTA and PPTA-MWNTs/PPTA were grey and olive-green in colour respectively. The fact that the materials were markedly different in appearance gave some preliminary indication that the MWNTs had been distributed differently within the polymer matrix. Optical images of the p-MWNTs/PPTA and PPTA-MWNTs/PPTA composites at 500× magnification show macroscopic aggregates of MWNTs in the case of the p-MWNTs (black regions in FIG. 6a), which were absent in the case of the PPTA-MWNTs (FIG. 6b).

SEM images of the materials deposited onto a piece of silicon wafer indicated that large aggregates of MWNTs existed on top of large PPTA regions in the case of the p-MWNTs (FIG. 6c). While in the case of the PPTA-MWNTs, individual MWNTs were observed to be embedded within the PPTA matrix, and were not found as aggregates within the material (FIG. 6d). The entire morphology of the samples was notably different as can be seen from the SEM images. We speculate that in the case of the p-MWNTs, PPTA were formed independently from the MWNTs that were present. In the case of the PPTA-MWNTs, PPTA-MWNTs were found to be embedded within the Kevlar matrix which exhibits markedly different grain size and morphology owing to the size regime of the MWNTs that the PPTA had formed around. FIGS. 6 e and f, show images of the materials at higher magnification which clearly show the p-MWNT aggregates in the case of the p-MWNTs/PPTA (e) and individual PPTA-MWNTs protruding from within sheets of the PPTA material (f). We hypothesize that in the latter case, that this is possible due to the intrinsic interaction between the materials on account of their identical surface chemistry.

Raman Spectroscopy of Composite Materials

Figure 7A:
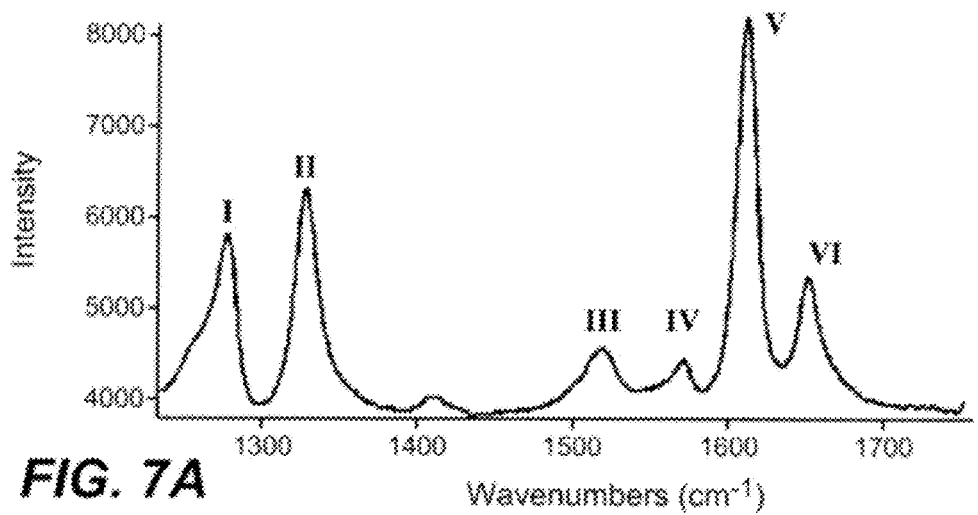
FIG. 7a-c is a set of Raman spectra of 7a) a PPTA region within the p-MWNTs/PPTA composite, 7b) an aggregate of p-MWNTs within the p-MWNTs/PPTA composite, and 7c) a representative area of the PPTA-MWNT/PPTA composite.
Figure 7B:
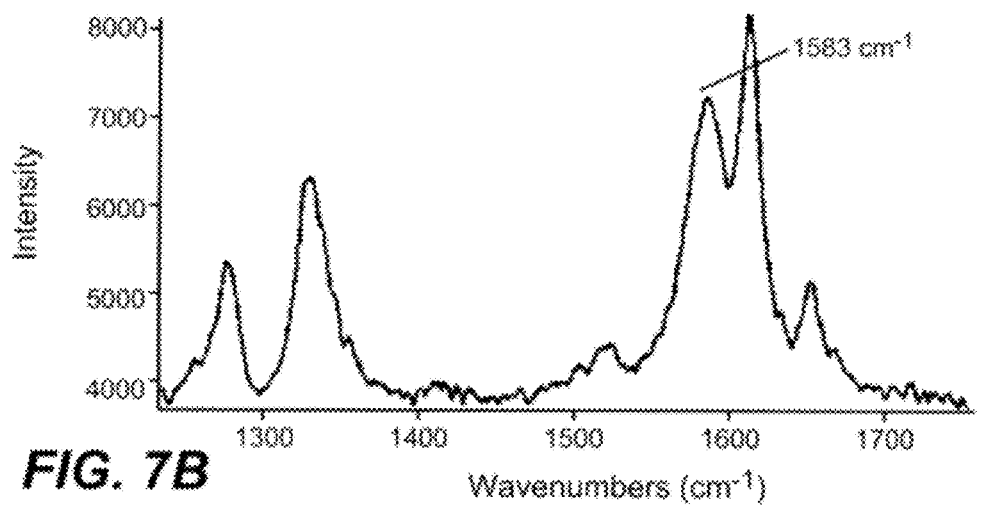
Figure 7C:
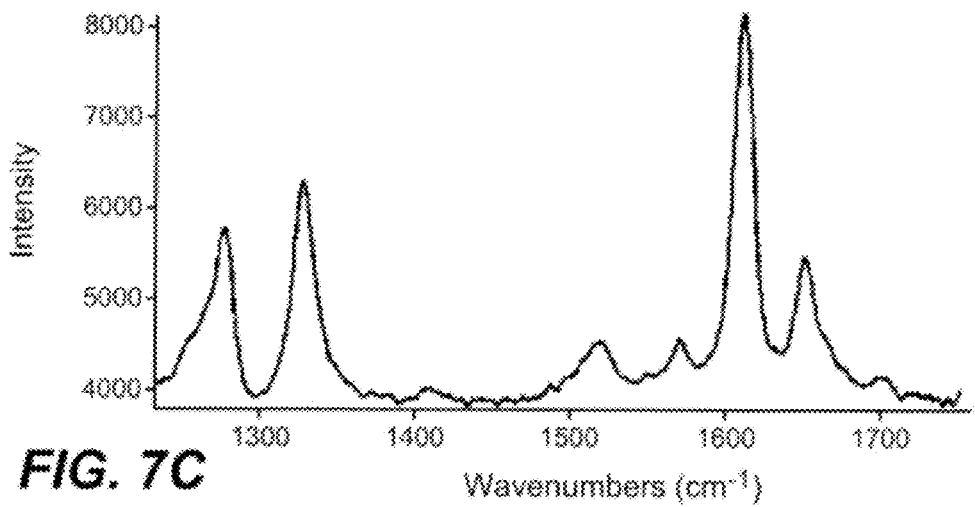
Figure 8A:
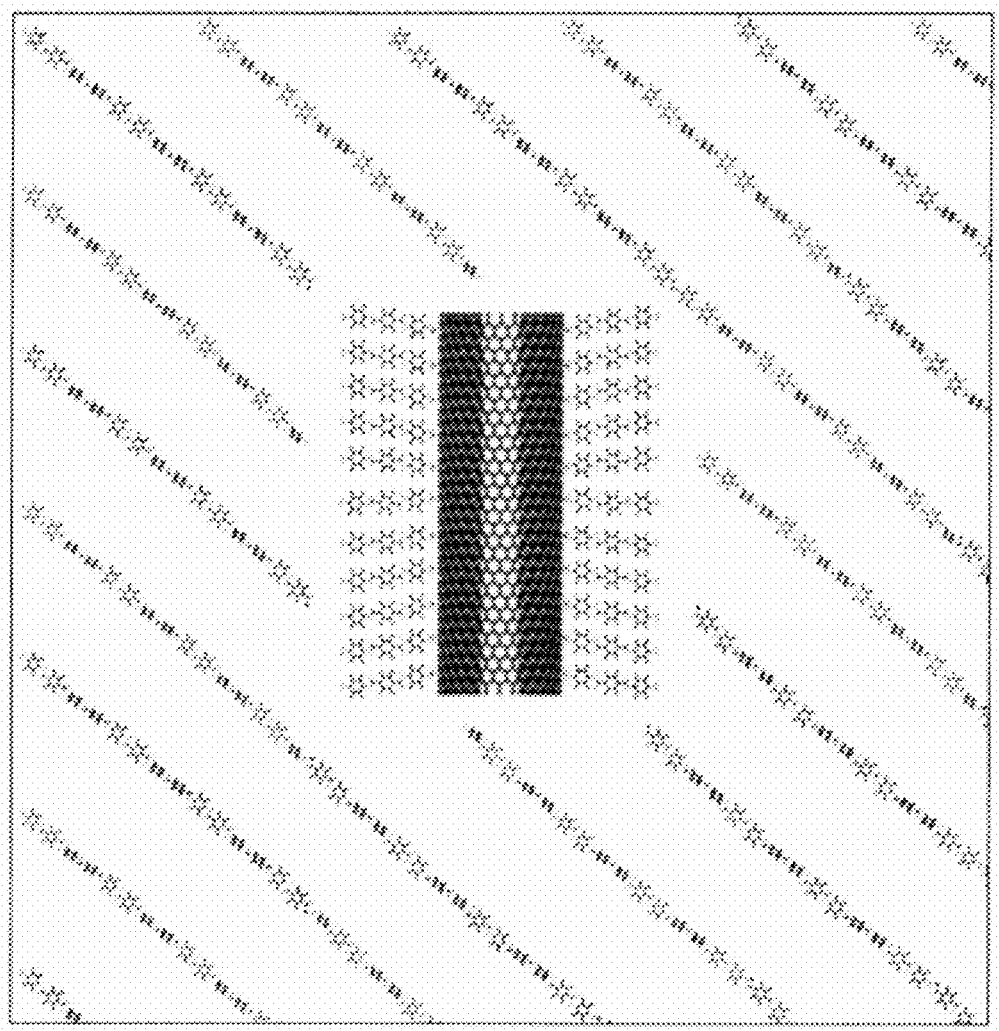
FIG. 8a is a schematic drawing of multi-walled carbon nanotubes (MWNTs) covalently functionalized with oligomeric units of poly-p-phenyleterphtalamide (PPTA), ("Kevlar"® aramid fiber) depicted within sheets of a liquid crystal PPTA matrix.
Figure 8B:
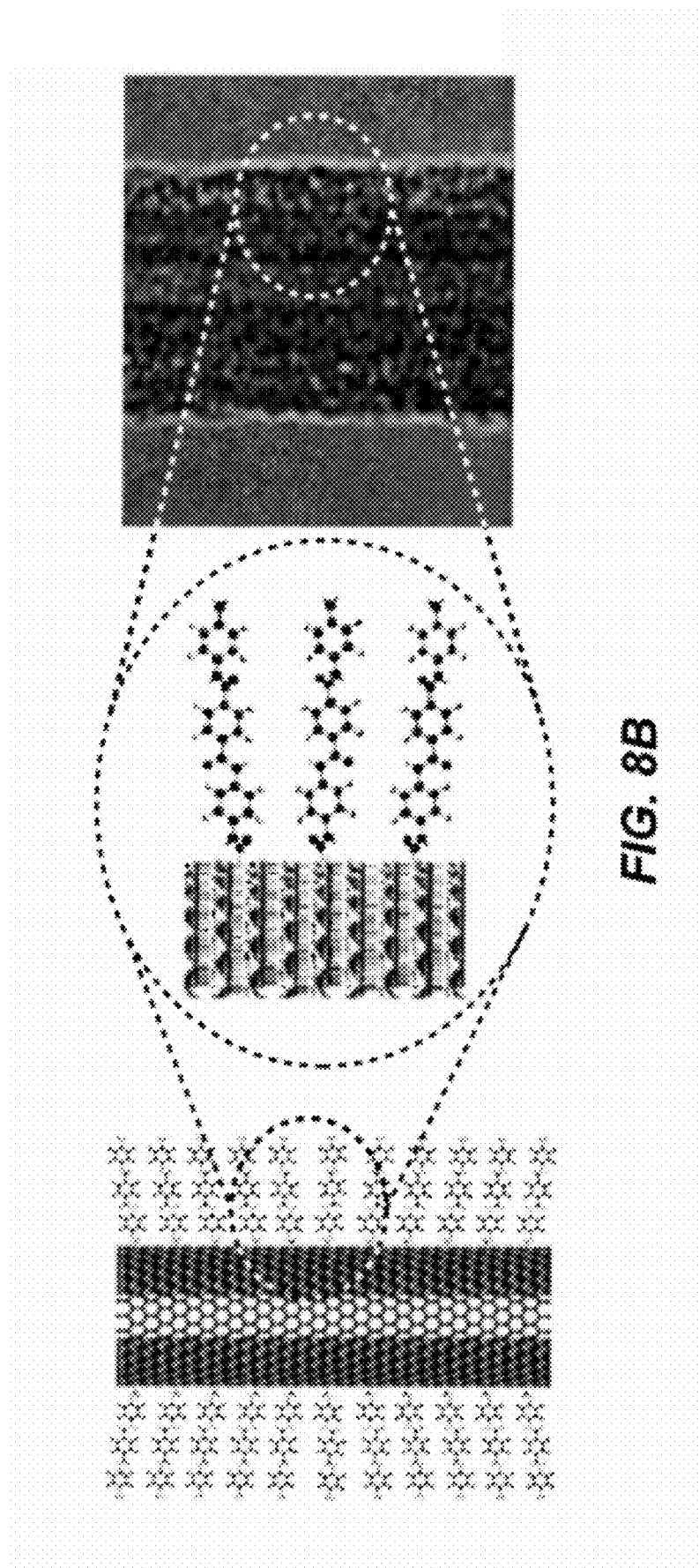
FIG. 8b is a figure relating a schematic representation of a TEM image.

Raman mapping of the composite materials also was used to spectroscopically identify the regions in the MWNTs/PPTA composites (λ=514.5 nm). In the case of the p-MWNT/PPTA composite, FIG. 7a shows the Raman bands corresponding to a region of PPTA material, as indicated by the optical image in the inset. The bands labeled I-VI correspond exactly with values reported in the literature for PPTA.[33] FIG. 7b shows the bands corresponding to an aggregate of p-MWNTs within the PPTA matrix as shown in the inset. Clearly evident is the appearance of a band at 1583 cm$^{-1}$ which is identified at the G-band characteristic of MWNTs. Such regions were indistinguishable in the case of the PPTA-MWNTs/PPTA material, whose spectrum was dominated by the PPTA bands, FIG. 7c. It is indeed gratifying that bands due to MWNTs are not observed in this latter case, corresponding with good integration and dispersion of MWNTs within the PPTA matrix.

Alternative Preparation of DAPPT by Coupling with 3-Mers

Overview

Figure 9:
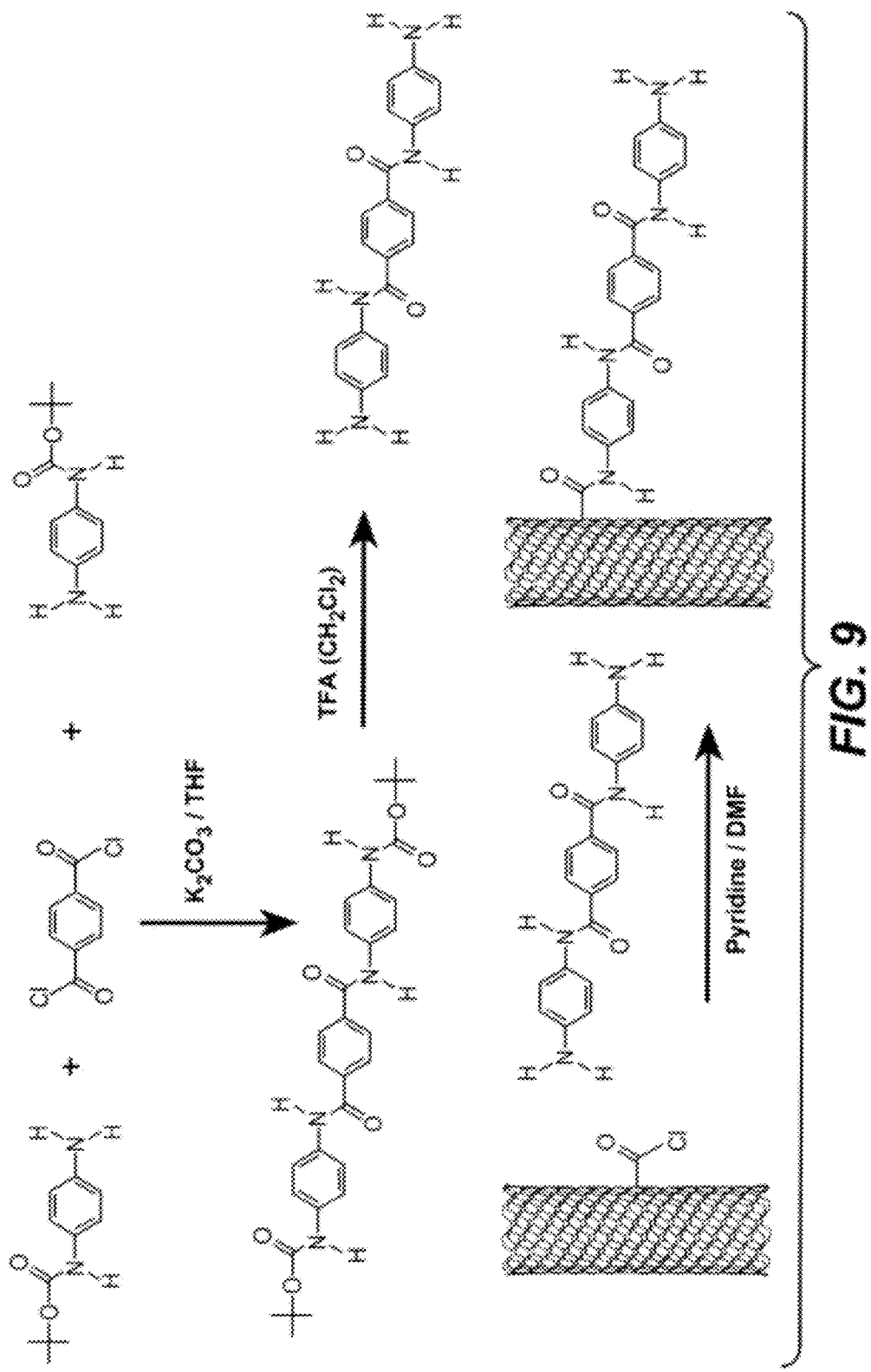
FIG. 9 is a reaction scheme of Boc-protected-PDA and TPC molecules to form protected 3-mer, deprotected to yield diamino-polyparaphenylen terpthalamide (DAPPT) and in II, the coupling of DAPPT oligomer with COCL-MWNTs to form PPT-functionalized MWNTs.

The functionalization of MWNTs with PPPT oligomer was also achieved by the amide formation between acid-chloride functionalized MWNTs the amine terminated PPPT 3-mer molecules, as shown in FIG. 9. The preparation of acid chloride MWNTs has been described previously. Briefly, it involves the strong acid oxidation of MWNTs in concentrated nitric acid followed by treatment with acidified potassium permanganate to ensure oxidation of keto and hydroxyl groups to maximise the concentration of carboxylic acid groups at the surface of the MWNTs. Subsequent treatment of carboxy-MWNTs with thionyl chloride converts the carboxylic acid groups to the acid-chloride.

Di-Amine-Polyaramid Oligomer:

Diamino-polyparaphenylene tereththalamide (DAPPPT) was prepared by coupling the Boc-protected p-phenylenediamine (PDA) with the di-acylchloride arene: terephthaloyl chloride (TPC), (2:1), followed by deprotection using standard Boc deprotection conditions (TFA in $CH_2Cl_2$) to yield the desired 3-mer molecule. Characterization of the 3-mer molecule by $^1$H-NMR, FTIR, and UV-vis spectroscopy was performed (as described in the supporting information). Exposure of dry acid-chloride-MWNTs to a solution of DAP-PPT in DMF facilitates the coupling of the 3-mer to the surface of the MWNTs via amide formation (FIG. 9). Upon addition of the DAPPPT oligomer solution to the acid-chloride-MWNTs, the flask was briefly sonicated to facilitate the dispersion of the MWNTs. The reaction mixture immediately turned from yellow to a dark green colour as a result of the MWNTs dispersed in solution. Upon further stirring, the reaction mixture turned deep black indicating complete solubilisation of the MWNTs.

FIG. 9 shows the reaction of Boc-protected-PDA and TPC molecules to form protected 3-mer, deprotected to yield diamino-polyparaphenylene terephthalamide (DAPPPT). FIG. 9. Shows coupling of DAPPPT oligomer with COCL-MWNTs to form PPPT-functionalized-MWNTs.

Following the reaction, extensive filtration and washing of the MWNTs, the PPPT-functionalized-MWNTs were readily suspended in DMF without the need for sonication. This indicates a distinct change in the surface chemistry of the MWNTs and also indicates that cross-linking of MWNTs has not occurred between the diamine-PPPT oligomers and adjacent MWNTs. This is ensured by using a large excess of DAPPPT for the reaction thus precluding aggregation of the MWNTs and maximising the covalent binding of oligomers at acid-chloride functional groups on the surface of the MWNTs. It is also noted that on account of the shortness and rigidity of the DAPPPT molecules, that simultaneous head and tail binding of the amine groups would be extremely unlikely.

Characterization of PPPT-functionalized MWNTs

PPPT-functionalized-MWNTs were characterized using (Fourier-transform-Infrared) FTIR, UV-Vis, and Raman Spectroscopy. The FTIR spectrum of pristine MWNTs is relatively featureless (data not shown). Weak, broadened bands between 1750 $cm^{-1}$ and 1550 $cm^{-1}$ cm may be attributed to keto- and carboxy-carbonyl absorption resulting from functional groups occurring at defects following synthesis. A broad spread of such absorptions indicates heterogeneity of the surface environment of such groups. The spectrum of the DAPPPT molecule shows bands at 1690 $cm^{-1}$ and 1643 $cm^{-1}$ due to the amide I C=O in both hydrogen bound and free states respectively (data not shown). The amino N—H and amide II N—H bands are seen at 1604 $cm^{-1}$ and 1535 $cm^{-1}$, while the aromatic C=C stretching vibration is seen as a sharp band at 1516 $cm^{-1}$. In the spectrum of the PPPT-functionalized-MWNTs (data not shown), these bands are also evident. The amide I C=O band is seen at 1643 $cm^{-1}$. The Amide II N—H band has broadened and shifted to 1545 $cm^{-1}$ which suggests a covalent bond to the lattice of the MWNT, while the aromatic C=C stretch is seen at 1512 $cm^{-1}$. The presence of the bands associated with the DAPPPT molecule, along with the shift of the Amide II band and the absence of the hydrogen bound form of the Amide I band give good evidence for the covalent attachment of the DAPPPT molecules at the surface of the MWNTs.

UV-vis spectroscopy was used to characterize the PPPT-functionalized-MWNTs. The spectrum of pristine-MWNTs exhibits a featureless scattering absorption profile typical of MWNTs while the spectrum of the DAPPPT 3-mer molecule exhibits an absorption maximum at wavelength=320 nm, with a broad shoulder in the region of wavelength=350 nm (data not shown). In contrast to pristine-MWNTs, PPPT-MWNTs exhibit significant absorption (data not shown). A maximum at wavelength=315 nm and a shoulder at wavelength=355 nm correspond with the absorption of the DAP-PPT molecule. Notably, a blue-shift of the principle absorption maximum from wavelength=320 nm to wavelength=315 nm, along with resolution of a distinct shoulder at wavelength=355 nm suggest a distinct change in the environment of the molecule, namely; the covalent attachment of the DAP-PPT molecule to the surface of the MWNTs to yield PPPT-functionalized-MWNTs.

The functionalization of MWNTs was also investigated using Raman Spectroscopy. Multiple reports exist describing the Raman spectra of functionalized SWNTs and MWNTs. MWNTs typically exhibit D- and G-band peaks indicative of the disorder-induced and the tangential-modes respectively, while a D'-band which is known to be affected by disorder in the nanotube lattice may be observed adjacent to the G-band peak. In the spectra of pristine-MWNTs (FIG. 10), the D-band is observed at 1326 $cm^{-1}$, while the G-band peak is observed at 1581 $cm^{-1}$ with a D' shoulder at 1613 $cm^{-1}$. The D- to G-band intensity ratios ($I_D/I_G$) is 0.84, which corresponds with the report of Gao and co-workers (0.81).[R] In the spectrum of carboxy-MWNTs (FIG. 10b), the D-band is observed at 1327 $cm^{-1}$, while the G-band at 1574 $cm^{-1}$ has significantly decreased in intensity yielding a $I_D/I_G$ ratio of 2.44. The D'-band has become more prominent and is clearly resolved at 1608 $cm^{-1}$. In the spectrum of PPPT-MWNTs, the D- and G-band are observed at 1328 $cm^{-1}$ and 1576 $cm^{-1}$ respectively, while the D'-band is observed at 1609 $cm^{-1}$. Notably, the intensity of the D-band is decreased yielding a $I_D/I_G$ ratio of 1.66, (as summarized in the Table 1).

TABLE 1

Figure 10:
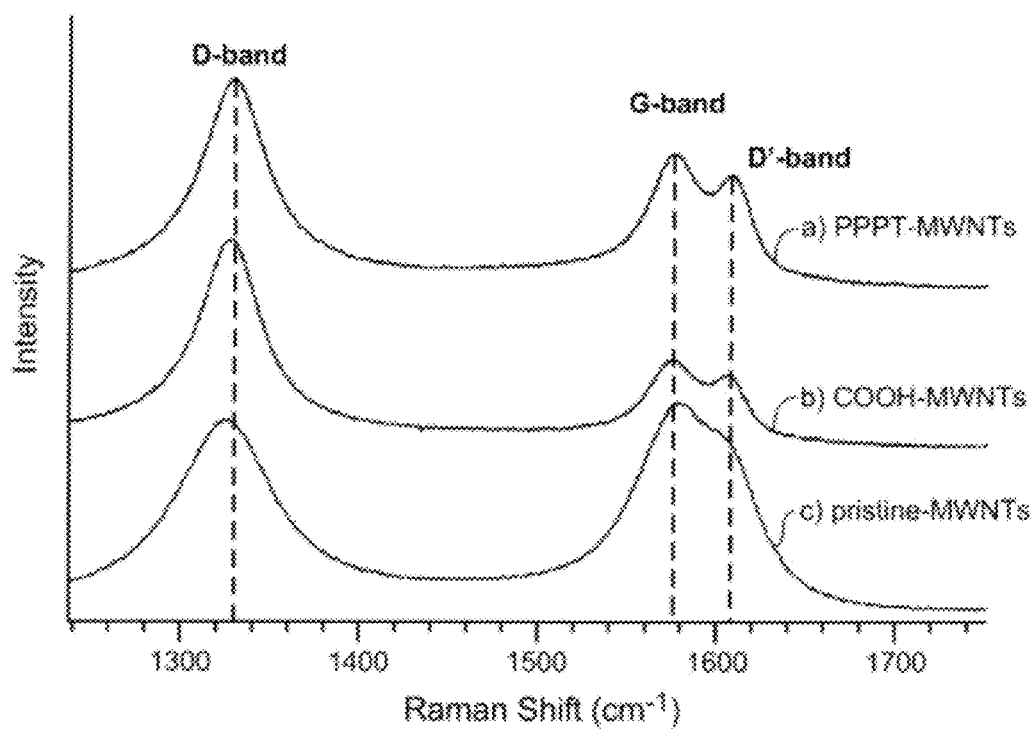
FIG. 10a-c is a set of Raman spectra of 10a) pristine-MWNTs, 10b) COOH-MWNTs and 10c) PPPT-MWNTs.

Raman peak frequencies corresponding to spectra in FIG. 10.

|  | D-band | G-band | D'-band | Intensity ratio ($I_D/I_G$) |
|---|---|---|---|---|
| Pristine-MWNTs | 1326 $cm^{-1}$ | 1581 $cm^{-1}$ | 1613 $cm^{-1}$ | 0.84 |
| COOH-MWNTs | 1327 $cm^{-1}$ | 1574 $cm^{-1}$ | 1608 $cm^{-1}$ | 2.44 |
| PPPT-MWNTs | 1328 $cm^{-1}$ | 1576 $cm^{-1}$ | 1609 $cm^{-1}$ | 1.66 |

Raman analysis of functionalized-MWNTs indicates that following oxidative modification of pristine-MWNTs the nanotube lattice is substantially perturbed as indicated by the decrease in the G-band peak and resolution of the D'-band; with a change in $I_D/I_G$ ratio from 0.84 to 2.44, suggestive of extensive functionalization of the surface of the MWNTs. Following PPPT-oligomer functionalization of the MWNTs, the $I_D/I_G$ ratio is relaxed from 2.44 to 1.66. This may be the result of the covalent attachment of relatively bulky substituent groups to the surface of the MWNTs which influence the Raman allowed transitions. A further study is currently underway to investigate substituent effects on functionalized-MWNTs.

Demonstration of Chemical Functionality of PPT-Functionalized MWNTs

Figure 11A:
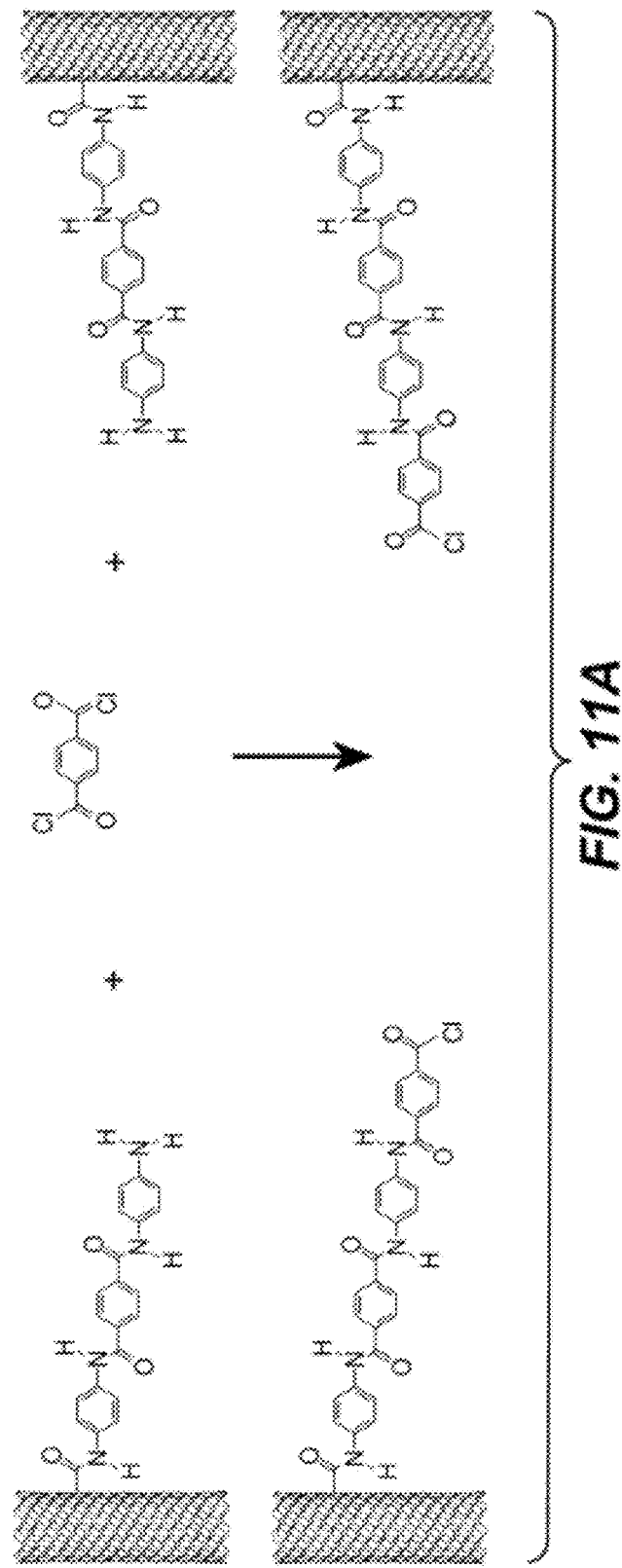
FIG. 11a-b is a schematic showing 11a) addition of TPC molecules to terminate the PPT oligomers at the surface of the MWNTs, and 11b) addition of PPT oligomer to facilitate the crosslinking of the PPT-MWNTs.

Characterization of the PPPT-functionalized-MWNTs using FTIR, UV-vis, and Raman analysis supports the assertion that the PPPT oligomers are covalently bound to the surface of the MWNTs. To demonstrate the chemical functionality of the PPPT-functionalized-MWNTs, cross-linking of the PPPT-MWNTs was performed. This was achieved by firstly activating the amine-terminated PPPT-oligomers at the surface of the MWNTs by exposure to terephthaloyl chloride (TPC) molecules (FIG. 11a). TPC was added to a stirring suspension of the PPPT-MWNTs in DMF and allowed to stir for two minutes to facilitate the coupling of the TPC molecules via amide formation. To cross-link the acid-chloride terminated PPPT-MWNTs, DAPPPT was added to the stirring solution and allowed stir for 30 s (FIG. 11).

Figure 11B:
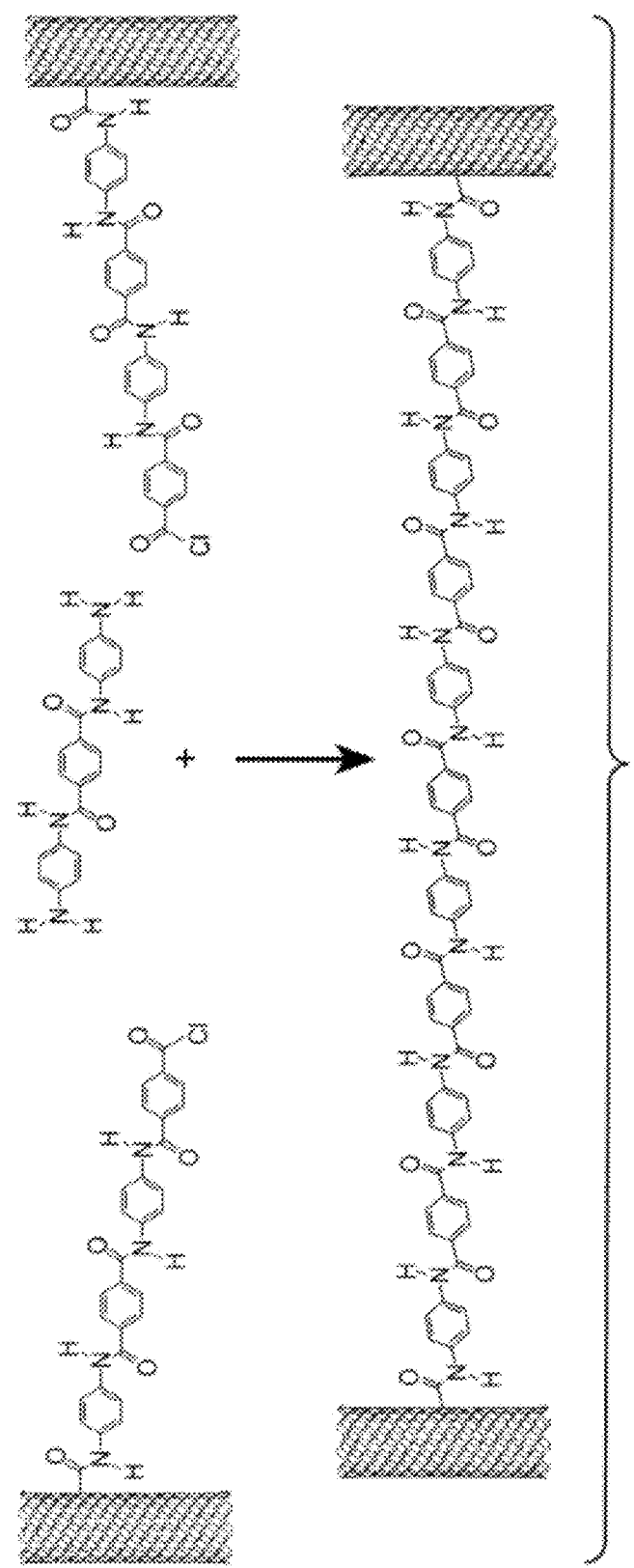

The addition of the DAPPPT oligomers was expected to facilitate cross-linking between adjacent PPPT-MWNTs as illustrated in FIG. 11b. Following addition of the DAPPPT, the deep black suspension immediately began to clear as the MWNTs precipitated from solution (photographs not shown).

It was evident from visual observation that unmodified-MWNTs exhibit poor solubility in DMF whereas PPPT-MWNTs exhibit excellent solubility. In contrast, cross-linked-PPPT-MWNTs form an insoluble precipitate. It is believed that the addition of DAPPPT oligomer molecules result in the formation of an extended PPPT or Kevlar structure extending from the surface of the MWNTs, i.e. Kevlar-cross-linked MWNTs. The exact nature of the PPPT structures cannot be known, however it can be speculated that the structures may be Scenario I: covalent PPPT bridges between MWNTs (FIG. 12a), Scenario II: overlapping PPPT-MWNT structures (FIG. 12b), Scenario III: cross-linked structures of PPPT-MWNTs and interstitial PPPT chains (FIG. 12c), or a combination of all three. This overlapping and cross linking is further illustrated schematically in FIG. 13.

Figure 12:
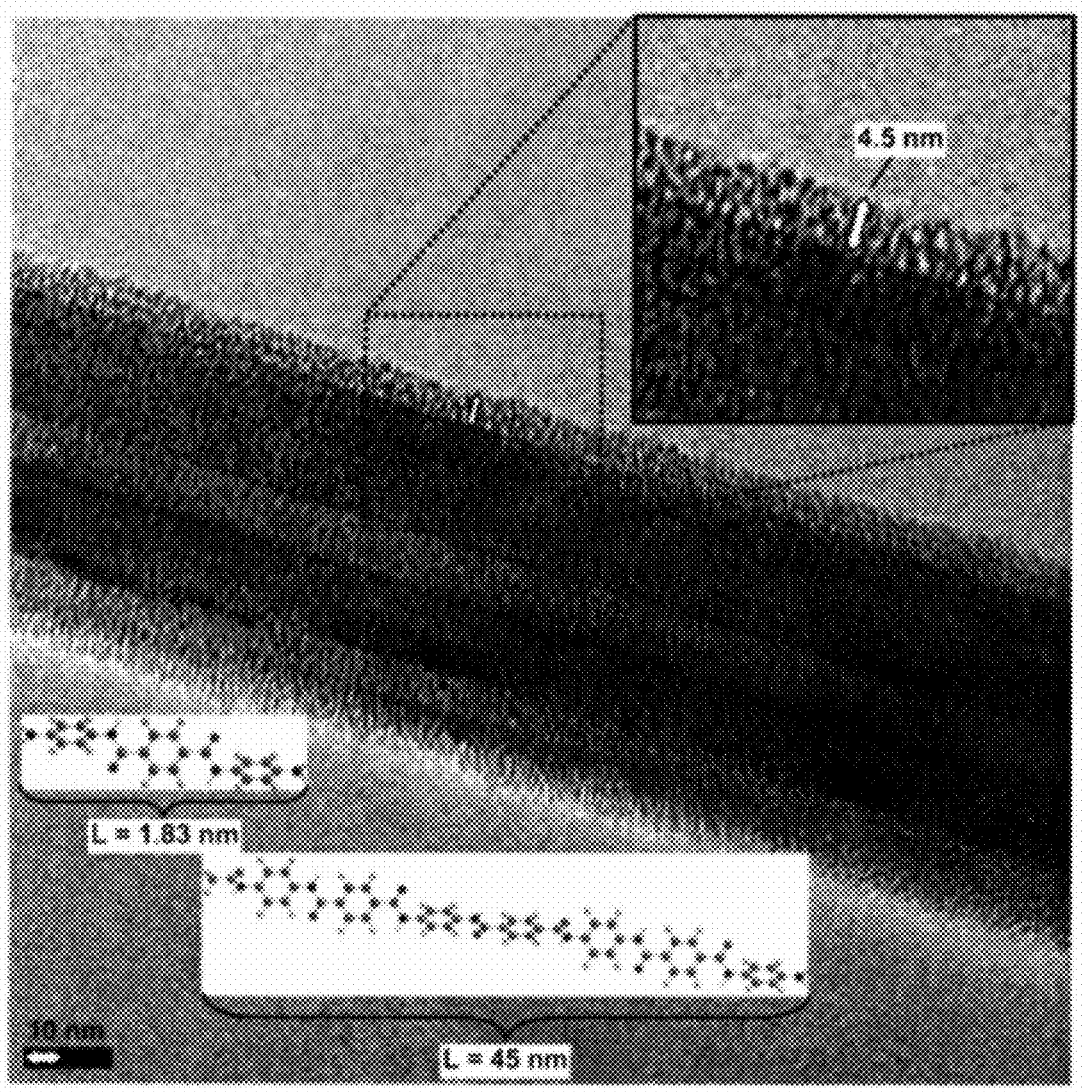
FIG. 12 is a TEM image of PPPT/Kevlar aramid fiber cross-linked MWNTs, inset showing outfield image of MWNT aggregate.
Figure 13A:
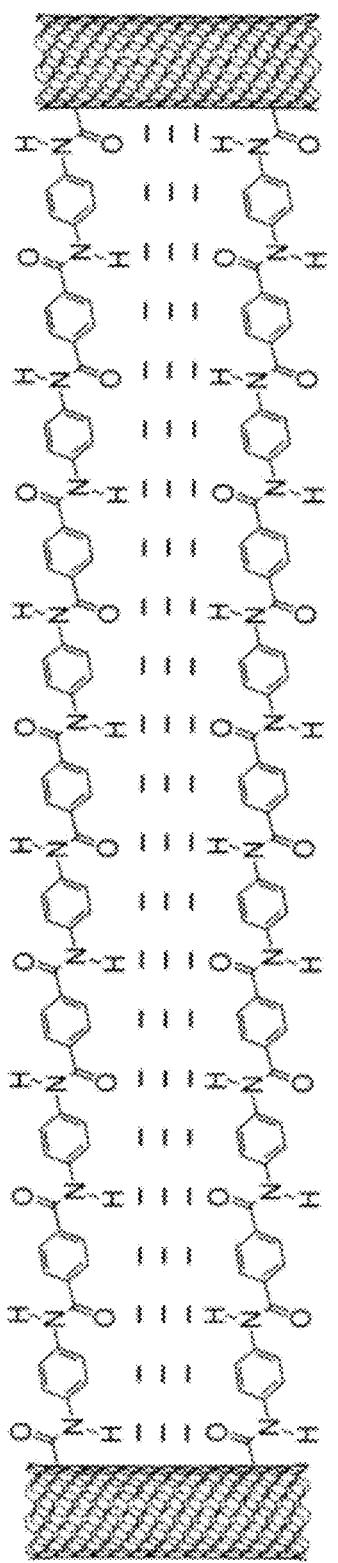
FIG. 13 a-c shows PPPT/Kevlar® aramid fiber cross-linked MWNTs: 13a) mediated by covalent-PPPT chains, 13b) overlapping-MWNT-bound PPPT chains, 13c) overlapping-MWNT and free PPT/PPPT chains.
Figure 13B:
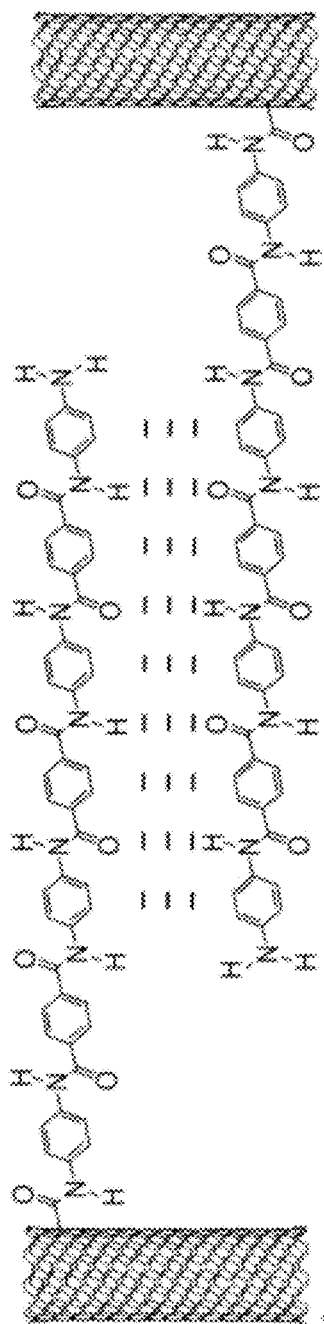
Figure 13C:
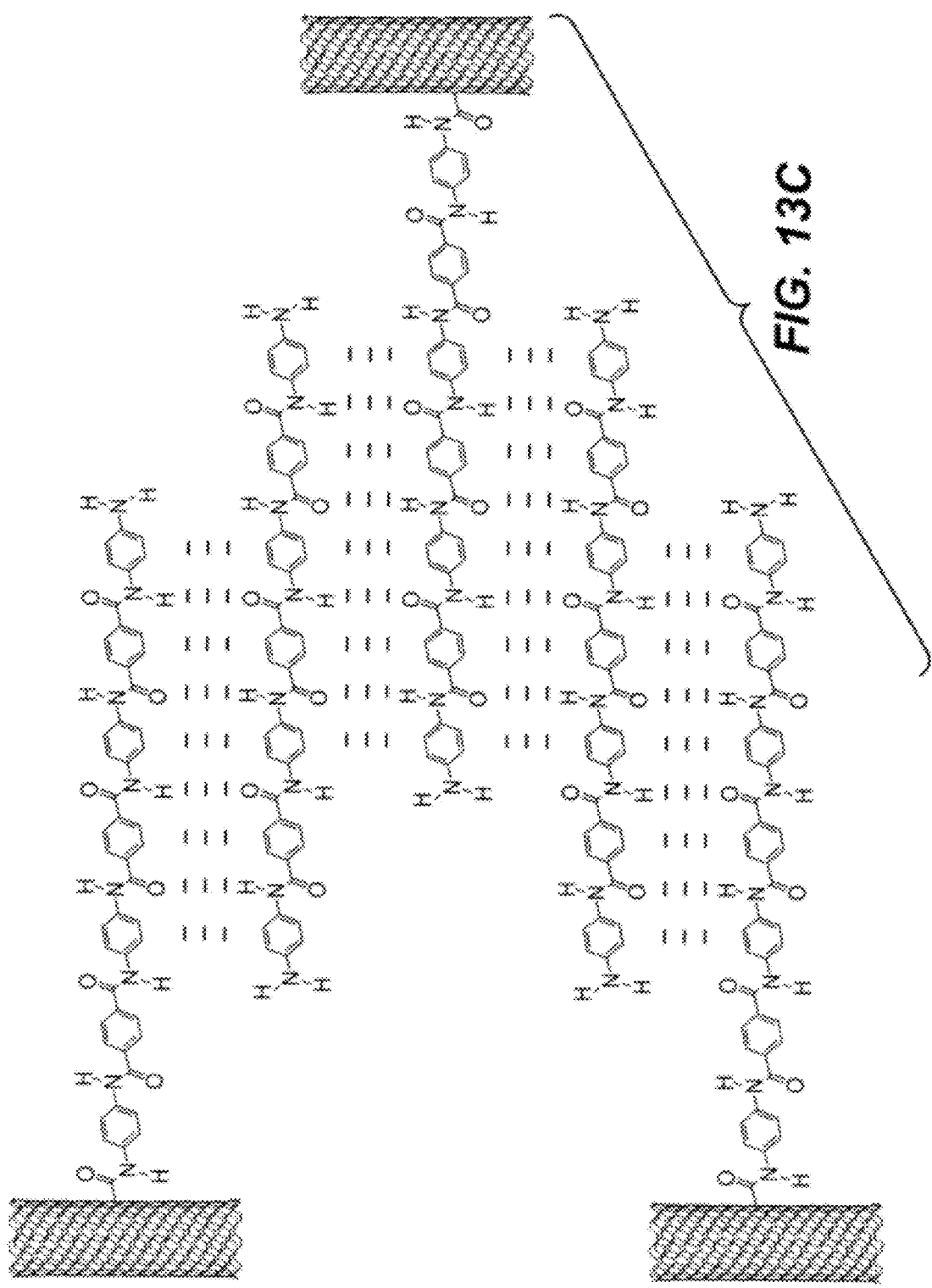

The nature of the interactions between structures is believed to be either covalent, or a combination of pi- and H-bonding interactions, or both. It is noted that as a result of the addition of both TPC molecules and PPT oligomers, the formation of PPPT chains would be expected as well as covalent and overlapping interactions between PPT-MWNTs. Consequently, it would be expected that a highly complex combination of scenarios would almost certainly be expected to exist. Analysis of the cross-linked MWNTs using TEM reveals a tangled mass of MWNTs covered in a thick organic layer (FIG. 12a). Notably, the TEM image shows that the sample consists predominantly of a tangled mass of nanotubes and not simply a mass of nanotubes imbedded within a polymer matrix. This is encouraging as it suggests that the aggregation of the nanotubes is dictated by the surface chemistry of the functionalized MWNTs, where cross-linking is triggered by the addition of the bi-functional PPT oligomer molecules. A HR-TEM image of a single tube, (FIG. 12b), shows a uniform coating of organic material at the surface of the tube, with a thickness of ~4.5 nm. It is worthy to note that the thickness of the organic layer corresponds with the length of two PPT oligomer units together with a TPC linker, as illustrated by the inserts in FIG. 6b. In this situation, the addition of TPC and PPT to an isolated PPT-MWNT results in the addition of the molecules extending from the surface of the MWNT, thus accounting for the thickness of organic material observed.

Thermo Gravimetric Analysis (TGA) was used to quantify the amount of organic material at the surface of PPT-MWNTs and PPPT-cross-linked-MWNTs. As the ability to control the surface chemistry of nanotubes is the focus of this work, cross-linking of MWNTs using PPPT employing two additional strategies were also performed for comparative purposes. The first of these strategies involved the sequential coupling of PPT oligomers and TPC molecules to the surface of acid-chloride-MWNTs in solution. The second strategy involved the coupling of PPT and TPC molecules to acid-chloride-MWNTs which had been immobilised in a mat-like structure using a filtration apparatus. It is noted that the TGA data was obtained by taking the derivative of the weight change with respect to temperature (d(wt)/dT) and normalising the organic proportion with respect to the CNT proportion.

TGA analysis of PPT-MWNTs (Sample A) indicated the organic material accounted for 45% of the sample (data not shown). This indicated that a significant proportion of the sample to be made up of the organic material and confirms the extensive functionalization of the surface of the MWNTs. It is also worthy to note that extensive washing and drying of the MWNTs was carried out to ensure a reliable analysis. Analysis of the MWNTs which had been cross-linked via grafting of PPT and TPC molecules to the surface of the acid-chloride-MWNTs (Sample B) indicated that 55% of the sample was organic material.

The increase in organic fraction in comparison to the PPT-MWNTs (45%) indicates that grafting of PPT and TPC molecules to the surface of the MWNTs had occurred. This was also evident from the formation of aggregates of the MWNTs following addition of grafting molecules to the stirring MWNT suspension. Sample C was formed by immobilizing acid-chloride-MWNTs in a mat-like structure using filtration apparatus. Sequential addition of solutions of PPT and TPC molecules through the filter was carried out to facilitate the addition and cross-linking of PPPT material between MWNTs. TGA analysis of the material gave an organic proportion of 72%. In this case, the grafting and cross-linking of PPPT material between MWNTs was believed to be much greater than that of grafting to MWNTs in solution (Sample B) due to the close packed 3-D mat-like structure and thus the direct physical proximity of adjacent MWNTs. Finally, TGA analysis of Sample D, PPPT-cross-linked MWNTs, as described in detail above, indicated that 83% of the sample was organic material. It is believed that the extremely good dispersion of the PPT-MWNTs in DMF facilitated an optimum density of TPC and PPT molecules coupled to the PPT-functionalized-MWNTs and in turn resulting in the cross-linking of the MWNTs by PPPT/Kevlar chains.

This example shows that MWNTs were functionalized with PPT-oligomer units. The functionalization procedure allows the functionalized MWNTs to be suspended in a solvent and furthermore that the PPT-functionalized-MWNTs are amenable to surface chemistry. The demonstration of the ability to cross-link the functionalized-MWNTs highlights the fact that the relatively inert surface chemistry of the pristine MWNTs has been fundamentally modified. It is this feature that demonstrates that the surface chemistry of MWNTs can be modified to be chemically identical to a host polymer matrix, in this case with an industrially relevant polymer; the polyaramid Kevlar.

Both the ability to suspend, MWNTs in a solvent and the ability for MWNTs to be chemically amenable to a host polymer matrix are seen as key factors which would enable the successful dispersion and integration of MWNTs to form polymer-nanotube composite materials. This work represents a basis for further studies involving the total integration of MWNTs as filler materials within polymer matrices to form advanced composites.

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference and contained herein, as needed for the purpose of describing and enabling the method or material referred to.

REFERENCES

1. Coleman, J. N.; Khan, U.; Blau, W. J. Carbon 2006, 44, 1624.
2. Baughman, R. H.; Zakhidov, A. A.; de Heer, W. A. Science 2002, 297, 787.
3. Gao, J.; Zhao, B.; Itkis, M. E.; Bekyarova, E.; Hu, H.; Kranak, V.; Yu, A.; Haddon, R. C. J. Am. Chem. Soc. 2006, 128, 7492.
4. Veedu, V. P.; Cao, A.; Li, X.; Ma, K.; Soldano, C.; Kar, S.; Ajayan, P. M.; Ghasemi-Nejhad, M. N. Nature Mat. 2006, 5, 457.
5. Li, Y.; Shimizu, H. Macromolecules 2009, 42, 2587.
6. Jeong, W.; Kessler, M. R. Chem. Mater. 2008, 20, 7060.
7. Zhang, X.; Cao, A.; Wei, B.; Li, Y.; Wei, J.; Xu, C.; Wu, D. Chem. Phys. Lett. 2002, 362, 285.
8. Raravikar, N. R.; Schadler, L. S.; Vijayaraghavan, A.; Zhao, Y.; Wei, B.; Ajayan, P. M. Chem. Mater. 2005, 17, 974.
9. Ci, L.; Suhr, J.; Pushparaj, V.; Zhang, X.; Ajayan, P. M. Nano Lett. 2008, 8, 2762.
10. Sekitani, T.; Noguchi, Y.; Hata, K.; Fukushima, T.; Aida, T.; Someya, T. Science 2008, 321, 1468.
11. Ma, W.; Liu, L.; Zhang, Z.; Yang, R.; Liu, G.; Zhang, T.; An, X.; Yi, X.; Ren, Y.; Niu, Z.; Li, J.; Dong, H.; Zhou, W.; Ajayan, P. M.; Xie, S, Nano Lett. 2009, 9, 2855.
12. Suhr, J.; Victor, P.; Ci, L.; Sreekala, S.; Zhang, X.; Nalamasu, O.; Ajayan, P. M. Nat. Nanotech. 2007, 2, 417.
13. Cao, A.; Dickrell, P. L.; Sawyer, W. G.; Ghasemi-Nejhad, M. N.; Ajayan, P. M. Science 2005, 310, 1307.
14. Velasco-Santos, C.; Martinez-Hernandez, A. L.; Fisher, F. T.; Ruoff, R.; Castaño, V. M. Chem. Mater. 2003, 15, 4470.
15. Gao, J.; Itkis, M. E.; Yu, A.; Bekyarova, E.; Zhao, B.; Haddon, R. C. J. Am. Chem. Soc. 2005, 127, 3847.
16. Coleman, J. N.; Khan, U.; Gun'ko, Y. Adv. Mater. 2006, 18, 689.
17. Zhu, J.; Kim, J.-D.; Peng, H.; Margrave, J. L.; Khabashesku, V. N.; Barrera, E. V. Nano Lett. 2003, 3, 1107.
18. Gao, C.; Zheng Jin, Y.; Kong, H.; Whitby, R. L. D.; Acquah, S. F. A.; Chen, G. Y.; Qian, H.; Hartschuh, A.; Silva, S. R. P.; Henley, S.; Fearon, P.; Kroto, H. W.; Walton, D. R. M. J. Phys. Chem. B 2005, 109, 11925.
19. Yao, Z.; Braidy, N.; Botton, G. A.; Adronov, A. J. Am. Chem. Soc. 2003, 125, 16015.
20. Baskaran, D.; Mays, J. W.; Bratcher, M. S. Angew. Chem. Int. Ed. 2004, 43, 2138.
21. O'Connor, I.; Hayden, H.; O'Connor, S.; Coleman, J. N.; Gun'ko, Y. K. J. Mater. Chem. 2008, 18, 5585.
22. O'Connor, I.; Hayden, H.; Coleman, J. N.; Gun'ko, Y. K. Small 2009, 5, 466.
23. Kwolek, S. L.; Morgan, P. W.; Gorenson, W. R. U.S. Pat. No. 3,063,966 (1966).
24. Tsang, S. C.; Harris, P. J. F.; Green, M. L. H. Nature 1993, 362, 520.
25. Ajayan, P. M.; Ebbesen, T. W.; Ichihashi, T.; Iijima, S.; Tanigaki, K.; Hiura, H. Nature 1993, 362, 522.
26. Tsang, S. C.; Chen, Y. K.; Harris, P. J. F.; Green, M. L. H. Nature 1994, 372, 159.
27. Hiura, H.; Ebbesen, T. W.; Tanigaki, K. Adv. Mater. 1995, 7, 275.
28. Burghard, M.; Krstic, V.; Duesberg, G.; Philipp, G.; Muster, J.; Roth, S. Syn. Metals 1999, 103, 2540.
29. Liu, J.; Rinzler, A. G.; Dai, H.; Hafner, J. H.; Bradley, R. K.; Boul, P. J.; Lu, A.; Iverson, T.; Shelimov, K.; Huffman, C. B.; Rodriguez-Macias, F.; Shon, Y.-S.; Lee, T. R.; Colbert, D. T.; Smalley, R. E. Science 1998, 280, 1253.
30. Jingsheng, B.; Anji, Y.; Shengqing, Z.; Shufan, Z.; Chang, H. J. Appl. Polym. Sci. 1981, 26, 1211.
31. Jorio, A.; Pimenta, M. A.; Souza Filho, A. G.; Saito, R.; Dresselhaus, G.; Dresselhaus, M. S. New J. Phys. 2003, 5, 139.1.
32. Badia, A.; Singh, S.; Demers, L.; Cuccia, L.; Brown, G. R.; Lennox, R. B. Chem. Eur. J. 1996, 2, 359.
33. Prasad, K.; Grubb, D. T. J. Appl. Polym. Sci. 1990, 41, 2189.

What is claimed is:

1. A nanostructure material, comprising:
   (a) a nanostructure having a defined pattern of covalently bonded surface atoms, wherein the nanostructure is selected from the group consisting of: MWNT, DWNT, SWNT, boron nitride nanotube, BxCyNz nanotube, graphene sheet, graphene ribbon, and silicon nanotube;
   (b) linking groups covalently bonded to a portion of said surface atoms; and
   (c) an aromatic polyamide attached by said linking groups to the nanostructure wherein the aromatic polyamide has between two and twenty monomer units.

2. The nanostructure material of claim 1 wherein the nanostructure having a defined pattern of covalently bonded surface atoms comprises a graphene surface structure.

3. The nanostructure material of claim 1 wherein the linking groups are selected from the group consisting of: a carboxylic acid, an ester, an acyl halide, an amine, an acyl amide, and a sulfide.

4. The nanostructure material of claim 1 wherein linking groups have the formula —C(=O), with a first carbon bond to the nanostructure and a second carbon bond to a monomer of the aromatic polyamide.

5. The nanostructure material of claim 4 wherein the second carbon bond is to an amine group on the monomer.

6. The nanostructure material of claim 5 wherein the monomer is p-phenylene diamine (PDA).

7. The nanostructure material of claim 1 wherein the aromatic polyamide comprises an aromatic diamine and an aromatic diacyl chloride.

8. The nanostructure material of claim 1 wherein the aromatic polyamide comprises alternating monomers of different chemical structure.

9. The nanostructure material of claim 1 wherein the aromatic polyamide comprises monomers of PDA and terephthaloyl chloride (TPC).

10. A composite material comprising a polyamide matrix in which is embedded a nanostructure material, comprising:
    (a) a nanostructure having a defined pattern of covalently bonded surface atoms;

(b) linking groups covalently bonded to a portion of said surface atoms; and
(c) synthetic oligomers attached by the linking groups to the nanostructure.

11. The composite material of claim 10 wherein the synthetic oligomers have the same structure as the polyamide matrix.

12. The composite material of claim 10 wherein the polyamide matrix comprises cross links to the synthetic oligomers.

13. The composite material of claim 12 wherein the cross links are hydrogen bonds between aromatic residues on the oligomers and the polyamide matrix.

14. The composite material of claim 10 wherein the nanostructure material is further defined by claim 9.

15. A method of preparing a nanostructure material, comprising a nanostructure having a defined pattern of covalently bonded surface atoms, linking groups covalently bonded to a portion of said surface atoms, and synthetic oligomers attached by the linking groups to the nanostructure, said method comprising the steps of:
(a) suspending nanostructures in a fluid;
(b) reacting the nanostructures in the fluid with a strong oxidizer for attachment of linking groups to form functionalized nanostructures;
(c) reacting the functionalized nanostructures with a first monomer unit to link the monomer unit to the linking groups and form a monomer-nanostructure; and
(d) adding a second monomer unit to said monomer-nanostructure under conditions to couple the second monomer unit to the first monomer unit form a copolymer after coupling.

16. The method of claim 15 wherein the first monomer unit and the second monomer unit independently comprise one-, two- or three-mers of monomer.

17. The method of claim 15 wherein the conditions that couple the second monomer unit to the first monomer unit comprise a condensation reaction.

18. The method of claim 15 wherein the first monomer unit is a monomer of an aromatic diamine.

19. The method of claim 15 where the second monomer unit is a monomer of an aromatic diacyl chloride.

20. The method of claim 15 wherein reacting with the first monomer unit and the second monomer unit is done as a mixture of monomer units to form a random copolymer.

21. The method of claim 15 further comprising the step of adding a pre-formed oligomer of 2 to 5 units to the nanostructure.

22. A nanostructure material, comprising:
(a) a nanostructure having a defined pattern of covalently bonded surface atoms;
(b) linking groups covalently bonded to at least 1% of said surface atoms; and
(c) one or more monomers of an aromatic polyamide attached by the linking groups to the nanostructure.

23. The nanostructure of claim 22 where the nanostructure is a carbon nanotube and the linking groups comprise carbonyl atoms.

* * * * *